US006849611B2

(12) United States Patent
Rosen et al.

(10) Patent No.: US 6,849,611 B2
(45) Date of Patent: Feb. 1, 2005

(54) IMPLANTATION OF BIOLOGICAL PACEMAKER THAT IS MOLECULARLY DETERMINED

(75) Inventors: Michael R. Rosen, New York, NY (US); Richard B. Robinson, Cresskill, NJ (US); Ira S. Cohen, Stony Brook, NY (US); Han-Gang Yu, Stony Brook, NY (US)

(73) Assignees: The Trustees of Columbia University in the City of New York, New York, NY (US); Research Foundation of State University of New York, Stony Brook, NY (US)

( * ) Notice: Subject to any disclaimer, the term of this patent is extended or adjusted under 35 U.S.C. 154(b) by 0 days.

(21) Appl. No.: 09/875,388

(22) Filed: Jun. 6, 2001

(65) Prior Publication Data

US 2002/0187948 A1 Dec. 12, 2002

(51) Int. Cl.$^7$ .............................................. A61K 48/00
(52) U.S. Cl. .................... 514/44; 435/455; 435/456; 424/93.2
(58) Field of Search ................................. 435/455, 456, 435/325; 424/93.2, 93.21; 514/44

(56) References Cited

U.S. PATENT DOCUMENTS

| 6,214,620 B1 | 4/2001 | John et al. .................. 435/455 |
| 6,231,518 B1 | 5/2001 | Grabek et al. .............. 600/508 |
| 2002/0155101 A1 | 10/2002 | Donahue et al. | |
| 2002/0187949 A1 | 12/2002 | Rosen et al. | |
| 2002/0188212 A1 | 12/2002 | Rosen et al. | |

FOREIGN PATENT DOCUMENTS

| WO | 0063434 | 10/2000 |
| WO | WO 00/63434 | * 10/2000 |

OTHER PUBLICATIONS

Griscelli et al., Human Gene Therapy, 1998 9:abstract, PubMed [online] Bethesda, MD USA: United States National Library of Medicine [retrieved on Mar. 25, 2004]. Retrieved from: PubMed.*
Rosenberg et al. Science, vol. 287, 2000, p. 1751.*
Moss, PACE, vol. 20, pp. 2058–2060, 1997.*
Verma, Nature, vol. 389, pp. 239–242, 1997.*
Anderson et al., Nature, vol. 392, pp. 25–30, Apr. 1998.*
Proenza et al. The Journal of Biological Chemistry, vol. 277, 5101–5109, 2002.*
Priori et al. Nature Medicine, vol. 6, pp. 1316–1318, 2000.*
Matsuo et al. (Disapperance of complete atrioventricular block after chemotherapy for malignant lymphomas, J. Cardiol, 1999, vol. 34, abstract) Medicine [online] Bethesda, MD USA: United States National Library of Medicine [retrieved on Jan. 23, 2003].*

Nattel, et al., "Arrhythmogenic ionic remodeling–Adaptive responses with maladaptive consequences," *Trends in Cardiovascular Medicine,* (2001), 11(7): 295–301; and (Exhibit 6).
Rubanyi, Gabor, "The future of human gene therapy," *Molecular Aspects of Medicine,* (2001), 22:113–142. (Exhibit 7).
DiFrancesco D: The cardiac hyperpolarizing–activated current, $I_f$: Origins and developments. *Prog. BiophysMol. Biol.* vol. 46, No. 3, 1985, pp. 163–183; (Exhibit 2).
Zhou Z and Lipsius SL: Effect of isoprenaline on $I_f$ current in latent pacemaker cells isolated from cat right atrium: ruptured vs. perforated patch whole–cell recording methods. *Pflugers Arch.* vol. 423, No. 5 Pt. 6, Jun. 1993, pp. 442–447; (Exhibit 3).
Thuringer D, et al.: A hyperpolarization–activated inward current in human myocardial cells. *JmolCell. Cardiol.* vol. 24, No. 5, May 1992, pp. 451–455; (Exhibit 4).
Porciatti F, et al.: Block of the pacemaker current $I_f$ in single human atrial myocytes and the effect of beta–adrenoceptor and A1–adenosine receptor stimulation. *Br Jpharmacol.* vol. 122, No. 6, Feb. 1991, pp. 963–969.
Yu, H, et al.: Pacemaker current exists in ventricular myocytes. *Circ. Res.* vol. 72, No. 1, Jan. 1993, pp. 232–236.; (Exhibit 5).
Cerbai E, et al.: The properties of the pacemaker current $I_f$ in Human Ventricular Myocytes are modulaed by Cardiac Disease. *Jmol. Cell Cardiol.* vol. 33, No. 3, Mar. 2001, pp. 441–448; (Exhibit 6).
DiFrancesco D: Generation and control of cardiac pacing: the pacemaker current. *Tends Cardiovasc. Med.* vol. 1, 1991, pp. 250–255.
Robinson RB, et al.: Developmental change in the voltage dependence of the pacemaker current, $I_f$, in rat ventricular cells. *Pflugers Arch.* vol. 433, 1991, pp. 533–535; (Exhibit 7).
Fares N, et al.: Characterization of a hyperpolarization–activated current in dedifferentiated adult rat ventricular cells in primary culture. *J. Physiol.* vol. 506, No. 1, Jan. 1, 1998, pp. 73–82; (Exhibit 8).
Cerbai E, et al.: Influence of postnatal–development on $I_f$ occurrence and properties in neonatal rat ventricular myocytes. *Cardiovasc. Res.* vol. 42, No. 2, May 1999, pp. 416–423; (Exhibit 9).

(List continued on next page.)

*Primary Examiner*—Scott D. Priebe
*Assistant Examiner*—Brian Whiteman
(74) *Attorney, Agent, or Firm*—John P. White; Cooper & Dunham LLP

(57) ABSTRACT

This invention provides for a method of inducing a current in the heart in a subject which comprises contacting a cell of the heart of a subject with a compound in a sufficient amount to induce a current in the cell of the heart of a subject. This invention also provides a method of treating a cardiac condition in a subject which comprises contacting a cell of the heart of the subject with a compound in an amount sufficient to increase the current expression of the cell, thereby treating the cardiac condition in the subject.

7 Claims, 25 Drawing Sheets

OTHER PUBLICATIONS

Cerbai E, et al.: Characterization of the hyperpolarization–activated current, $I_f$, in ventricular myocytes isolated from hypertensive rats. *J. Physiol.* vol. 481, No. 3, Dec. 15, 1994, pp. 585–591; (Exhibit 10).

Cerbai E, et al.: Characterization of the hyperpolarization–activated current, $I_f$, in ventricular myocytes from human failing heart. *Circulation.* vol. 95, No. 3, Feb. 4, 1997, pp. 568–571; (Exhibit 11).

Santoro B, et al.: Interactive cloning with the SH3 domain of the N–src identifies a new brain specific ion channel protein, with homology to Eag and cyclic nucleaotide–gated channels. *Proc. Natl. Sci. USA.* vol. 94, No. 26, Dec. 23, 1997, pp. 14815–14820; (Exhibit 12).

Ludwig A, et al.: A family of hyperpolarization–activated mammalian cation channels. *Nature.* vol. 383, No. 6685, Jun. 11, 1998, pp. 587–591; (Exhibit 13).

Santoro B, et al.: Identification of a gene encoding a hyperpolarization–activated pacemaker channel of brain. *Cell.* vol. 93, No. 5, May 29, 1998, pp. 717–729; (Exhibit 14).

Shi W, et al.: Distribution and Prevalence of hyperpolarization–activated cation channel (HCN) mRNA Expression in Cardiac Tissues. *Circ. Res.* vol. 85, No. 1, Jul. 9, 1999, pp. e1–e6; (Exhibit 15).

Ishii TM, et al.: Molecular characterization of the hyperpolarization–activated cation channel in rabbit heart sinoatrial node. *J. Biol. Chem.* vol. 264, No. 18, Apr. 30, 1999, pp. 12835–12839; (Exhibit 16).

Ludwig A, et al.: Two pacemaker channels from human heart with profoundly different activation kinetics. *EMBO J.* vol. 18, No. 9, May 4, 1999, pp. 2323–2329; (Exhibit 17).

Moosmang S, et al.: Cellular expression and functional characterization of four hyperpolarization–activated pacemaker channels in cardiac and neuronal tissues. *Eur. J. Biochem.* vol. 268, No. 6, Mar. 2001, pp. 1646–1652; (Exhibit 18).

Altomare C, et al.: Allosteric voltage–dependent gating of HCN channels. *Biophys. J.* vol. 80, 2001, pp. 241a.

Protas L, et al.: Chronic neuropeptide Y exposure increases L–type Ca current in neonatal rat cardiomyocytes. *Am. J. Physiol.* vol. 277, No. 3 Pt. 2, Sep. 1999, pp. H940–H946. (Exhibit 19).

Kuznetsov V, et al.: β 2–adrenergic receptor actions in neonatal and adult rat ventricular myocytes. *Circ. Res.* vol. 76, No. 1, Jan. 1995, pp. 40–52; (Exhibit 20).

Ellingston O, et al.: Adult rat ventricular myocytes cultured in defined medium: phenotype and electromechanical function. *Am. J. Physiol.* vol. 265, No. 2 Pt. 2, Aug. 1993, pp. H747–H754.

Ng P, et al.: An enhanced system for construction of adenoviral vectors by the two–plasmid rescue method. *Hwn. Gene Ther.* vol. 11, No. 5, Mar. 20, 2000, pp. 693–699; (Exhibit 21).

He TC, et al.: A simplified system for generating recombinant adenoviruses. *Proc. Natl. Acad. Sci. USA.* vol. 95, No. 5, Mar. 3, 1998, pp. 2509–2514; (Exhibit 22).

Santoro B, et al.: The HCN gene family: molecular basis of the hyperpolarization–activated pacemaker channels. *Ann. NY Acad. Sci.* vol. 868, Apr. 30, 1999, pp. 741–764; (Exhibit 23).

Accili EA, et al.: Properties and modulation of $I_f$ in newborn versus adult cardiac SA node. *Am. J. Physiol.* vol. 272, 1991, pp. H1549–H1552.

Qu J, et al.: Sympathetic innervation alters activation of pacemaker current $(I_{f) \, in \, rat \, ventricles}$. *J. Physiol.* vol. 526, No. 3, Aug. 1, 2000, pp. 561–569; (Exhibit 24).

Cui J, et al.: Gating of IsK expressed in Xenopus oocytes depends on the amount of mRNA injected. *Gen. Physiol.* vol. 104, No. 1, Jul. 1994, pp. 87–105; (Exhibit 25).

Guillemare, E, et al.: Effects of the level of mRNA expression on biophysical properties, sensitivity to neurotoxins, and regulation of the brain delayed–rectifier K+ channels Kv1.2. *Biochemistry.* vol. 31, No. 49, Dec. 15, 1992, pp. 12463–12468; (Exhibit 26).

Honore E, et al.: Different types of K+ channel current are generated by different levels of a single mRNA. *EMBO J.* vol. 11, No. 7, Jul. 1992, pp. 2465–2471; (Exhibit 27).

Honore E, et al.: Different types of K+ channel current are generated by different levels of a single mRNA. *EMBO J.* vol. 11, No. 7, Jul. 1992, pp. 2465–2471; (Exhibit 27).

DiFrancesco D, et al.: Direct activation of cardiac pacemaker channels by intracellular cyclic AMP. *Nature.* vol. 351, No. 6322, May 9, 1991, pp. 145–147; (Exhibit 29).

Kaupp UB, et al.: Molecular diversity of pacemaker ion channels. *Annu, Rev. Physiol.* vol. 63, 2001, pp. 235–257; (Exhibit 30).

Chang F, et al.; Effects of protein kinase inhibitors on canine Purkinje fibre pacemaker depolarization and the pacemaker current $I_f$. *J. Physiol.* vol. 440, 1991, pp. 367–384; (Exhibit 31).

Yu, H, et al.: Phosphatase inhibition by calyculin A increases $I_f$ in canine Purkinje fibers and myocytes. *Pflugers Arch.* vol. 422, No. 6, Mar. 1993, pp. 614–616; (Exhibit 32).

Accili EA, et al.: Differential control of the hyperpolarization–activated current ($I_f$) by intracellular cAMP and phosphatase inhibition. *J. Physiol.* vol. 491, 1996, pp. 115.

Ranjan R, et al.: Mechanism of anode break stimulation in the heart. *Biophys. J.* vol. 74, No. 4, Apr. 1998, pp. 1850–1863; (Exhibit 33).

Moroni A, et al.: Kinetic and ionic properties of the human HCN2 pacemaker channel. *Pflugers Arch.* vol. 439, No. 5, Mar. 2000, pp. 618–626; (Exhibit 34).

Santoro B, et al.: Molecular and functional heterogeneity of hyperpolarization–activated pacemaker channels in the mouse CNS. *Jneurosci.* vol. 20, No. 14, Jul. 15, 2000, pp. 5264–5275; (Exhibit 35).

Shi W, et al.: The distribution and prevalence of HCN isoforms in the canine heart and their relation to the voltage dependence of $I_f$. *Biophys. J.* vol. 78, 2000, pp. 353A.

Melman YF, et al.: Structural determinants of KvLQT1 control by the KCNE family of proteins. *J Biol Chem.* vol. 276, No. 9, Mar. 2, 2001, pp. 6439–6444; (Exhibit 36).

Tinel N, et al.: KCNE2 confers background current characteristics to the cardiac KCNQ1 potassium channel. *EMBO J.* vol. 19, No. 23, Dec. 1, 2000, pp. 6326–6330; (Exhibit 37).

Martens JR, et al.: Differential targeting of Shaker–like potassium channels to lipid rafts. *BiolChem.* vol. 275, No. 11, Mar. 17, 2000, pp. 7443–7446; (Exhibit 38).

Chauhan VS, et al.: Abnormal cardiac Na(+) channel properties and QT heart rate adaptation in neonatal ankyrin (B) knockout mice. *Circ. Res.* vol. 86, No. 4, Mar. 3, 2000, pp. 441–447; (Exhibit 39).

Gerhardstein BL, et al.: Proteolytic processing of the C terminus of the alpha (1C) subunit of L–type calcium channels and role of a proline–rich domain in membrane tethering of proteolytic fragments. *J. Biol. Chem.* vol. 275, No. 12, Mar. 24, 2000, pp. 8556–8563; (Exhibit 41).

Barbuti A, et al.: Action of internal pronase on the f–channel kinetics in the rabbit SA node. *J. Physiol.* vol. 520, No. 3, Nov. 1, 1999, pp. 737–744; (Exhibit 42).

Wainger BJ, et al.: Domains involved in cyclic nucleotide modulation of hyperpolarization–activated HCN channels. *Nature.* In Press, 2001.

Wahler GM: Developmental increases in the inwardly rectifying potassium current of rat ventricular myocytes. *Am. J. Physiol.* vol. 262, No. 5 Pt. 1, May 1992, pp. C1266; (Exhibit 43).

Abbott GW, et al.: MiRP1 forms $I_{kr}$ potassium channels with HERG and is associated with cardiac arrhythmia. *Cell.* vol. 97, No. 2, Apr. 16, 1999, pp. 175–187. (Exhibit 44).

Sanguinetti MC, et al.: Coassembly of KvLGQT1 and minK ($I_{SK}$) proteins to form cardiac $I_{SK}$ potassium channels. *Nature.* vol. 384, No. 6604, Nov. 7, 1996, pp. 80–83; (Exhibit 45).

Dixon JE and McKinnon D: Quantitative analysis of potassium channel expression in atrial and ventricular muscle of rats. *Circ. Res.* vol. 75, No. 2, Aug. 1994, pp. 252–260; (Exhibit 46).

Schagger H and von Jagow G: Tricine–sodium dodecyl sulfate–polyacrylamide gel electrophoresis for separation of proteins in the range from 1 to 100 Kda. *Analytical Biochem.* vol. 166, No. 2, Nov. 1, 1987, pp. 368–379; (Exhibit 47).

Hansen JE, et al.: Prediction of O–glycosylation of mammalian proteins:Specificity patterns of UDP–Gal-NAc:polypeptide N–acetylgalactosaminyltransferase. *Biochem. J.* vol. 308, No. 3, Jun. 15, 1995, pp. 801–813; (Exhibit 48).

Vassalle M, et al.: Pacemaker channels and cardiac automaticity In "Cardiac Electrophysiology. From Cell to Bedside", Eds. Zipes D and Jalife WB Saunders Co. Philadelphia, PA, 2000, pp. 94–103.

* cited by examiner

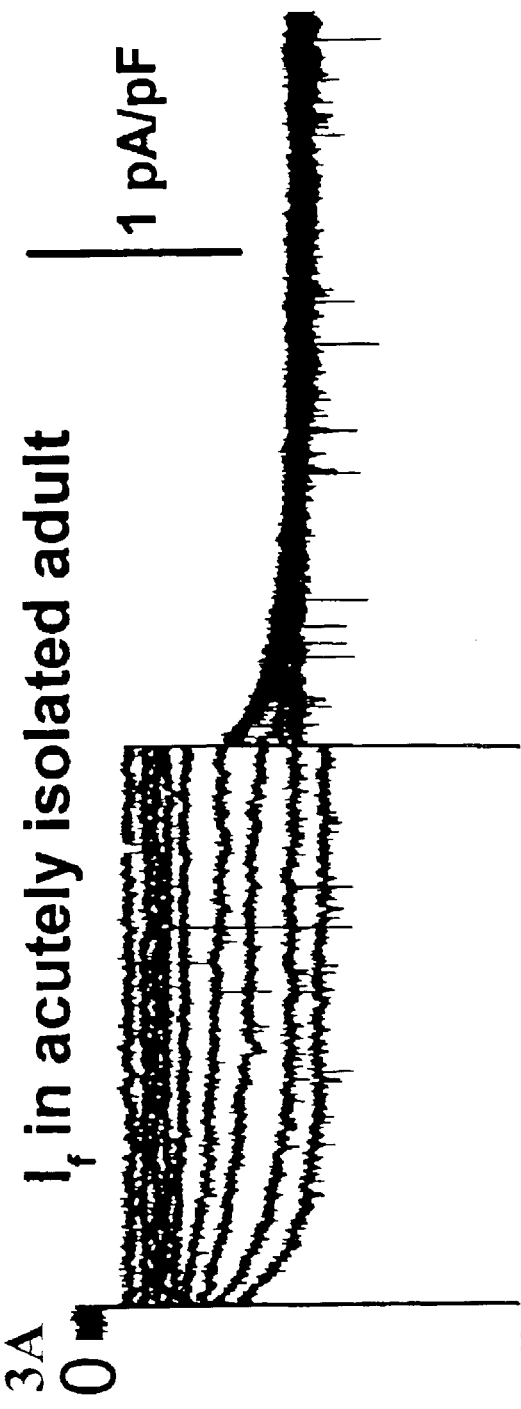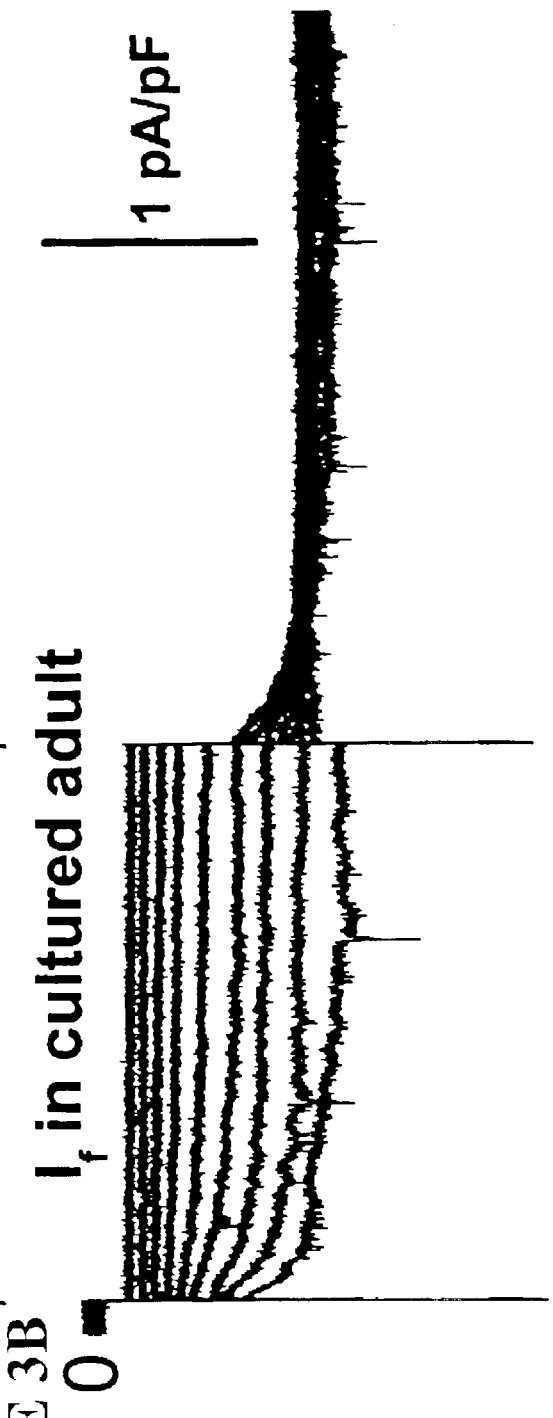
FIGURE 3A  $I_f$ in acutely isolated adult
FIGURE 3B  $I_f$ in cultured adult FIGURE 3C  $I_{HCN2}$ in cultured adult

IMPLANTATION OF BIOLOGICAL PACEMAKER THAT IS MOLECULARLY DETERMINED

The invention disclosed herein was made with Government support under NIH Grant Nos. HL-28958, HL-20558, NS-36658 from the National Institutes of Health. Accordingly, the U.S. Government has certain rights in this invention.

BACKGROUND OF THE INVENTION

The present invention relates to a biological heart pacemaker, and more importantly to an implantation in the heart of a biological pacemaker that is molecularly determined.

Throughout this application, various publications are referenced to by numbers. Full citations for these publications may be found at the end of the specification immediately preceding the claims. The disclosures of these publications in their entireties are hereby incorporated by reference into this application in order to more fully describe the state of the art to those skilled therein as of the date of the invention described and claimed herein.

The pacemaker current, $I_f$, is present in both automatic (1) and non-automatic (2–6) regions of the heart. Further, the threshold voltage of activation varies widely among cardiac regions, being least negative in the sinus node (e.g. in rabbit sinus node it is −40 mV (7)) and most negative in the ventricle (−108 mV or more negative, depending on species (5,8,9). Interestingly, the current activates at less negative voltages in the newborn ventricle (approximately −70 mV in rat (8,10)) and the diseased adult ventricle (approximately −70 mV threshold in aged hypertensive rat(11), −55 mV in failing human ventricle (12)) The molecular and cellular bases for the regional variability of activation voltages in the normal adult heart and the regulation of ventricular activation voltage by development and disease remain to be determined, but such understanding is critical to any future therapeutic application of the expressed current in myocardium.

SUMMARY OF THE INVENTION

This invention provides a method for the regulation of pacemaker function of cardiac muscle cells and/or specialized conducting fibers in the heart with HCN molecules (HCN 1, 2, or 4 isoforms of the pacemaker current $I_f$) and/or MiRP1 beta subunit, to produce a functioning site of impulse initiation that serves as the initiator of a heartbeat in settings where sinus node function is abnormal and or the sinus beat cannot activate the atria and or the ventricles normally.

This invention provides a method of treating a cardiac condition in a subject which comprises contacting a cell of the heart of the subject with a compound in an amount sufficient to increase the current expression of the cell, thereby treating the cardiac condition in the subject.

This invention also provides a method of inducing a current in the heart in a subject which comprises contacting a cell of the heart of a subject with a compound in a sufficient amount to induce a current in the cell of the heart of a subject, thereby inducing a current in the cell of the heart of the subject.

This invention further provides a method of increasing the heart rate in a subject which comprises contacting a cell of the heart of a subject with a compound in an amount sufficient to decrease the time constant of activation and deactivation of the cell of the heart, thereby increasing the heart rate in the subject.

This invention further provides a method of inducing a current in a cell which comprises contacting a cell with a compound in a sufficient amount to induce a current in the cell, thereby inducing a current in the cell.

This invention further provides a method of causing a contraction of a cell which comprises contacting the cell with a compound in an amount sufficient to induce a current required to cause a contraction of the cell, thereby causing a contraction of the cell.

This invention further provides a method of shortening the time required to activate and deactivate a cell which comprises contacting a cell with a compound in a sufficient amount to decrease the time constant of activation and deactivation of the cell, thereby shortening the time required to activate and deactivate the cell.

This invention further provides a method of changing the membrane potential of a cell which comprises contacting a cell with a compound in a sufficient amount to change the membrane potential of the cell, thereby changing the membrane potential of the cell.

This invention provides a method for the regulation of cardiac cells or specialized conducting fibers in the heart with HCN molecules, HCN 1, 2, or 4 isoforms of the pacemaker current, $I_f$, and or MiRP1 beta subunit, to produce a functioning site of impulse initiation that serves as the initiator of a heartbeat in settings where sinus node function is abnormal and or the sinus beat cannot activate the atria and or the ventricles.

BRIEF DESCRIPTION OF THE FIGURES

FIGS. 3A–D: current traces from adult ventricular myocytes. A: records from an acutely isolated myocyte. B: records from an adult myocyte maintained in culture for 48 hours. C: records from an adult myocyte infected with AdHCN2 and then maintained in culture for 48 hours. D: illustrates voltage protocol. Note the different vertical scale in (C).

DETAILED DESCRIPTION OF THE INVENTION

Figure 1A:
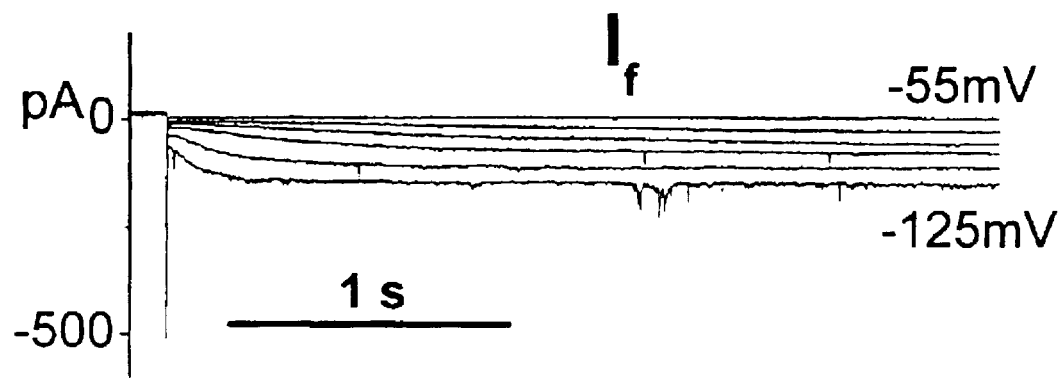
FIGS. 1A–C: current traces in neonatal ventricular culture of native $I_f$ and expressed HCN2 or HCN4. A: records from a control (non-transfected) myocyte. B: records from a myocyte co-transfected with pCI-mHCN2 and pEGFP-C1 using lipofectin. C: records from a myocyte co-transfected with pCI-mHCN4 and pEGFP-C1 using lipofectin. In all panels, the test voltage varied from −55 to −125 in 10 mV increments. Note, selected traces are omitted from panel (A) for clarity.

This invention provides a method of treating a cardiac condition in a subject which comprises contacting a cell of the heart of the subject with a compound in an amount sufficient to increase the current expression of the cell, thereby treating the cardiac condition in the subject.

This invention provides the above-described method, wherein the current is the pacemaker current.

This invention also provides the above-described method, wherein the subject is a mammal.

This invention provides the immediately preceding method, wherein the mammal is a human.

This invention further provides the above-described method, wherein the cell is a cardiac myocyte.

This invention further provides the above-described method, wherein the cardiac condition is a cardiac rhythm disorder.

This invention provides the immediately preceding method, wherein the cardiac rhythm disorder is selected from a group consisting of conductive block, complete atrioventricular block, incomplete atrioventricular block and sinus node dysfunction.

This invention further provides the above-described method, wherein the compound comprises a nucleic acid which encodes MiRP1.

This invention further provides the above-described method, wherein the compound comprises a nucleic acid which encodes an HCN channel.

This invention provides the immediately preceding method, wherein the HCN channel is HCN1.

This invention also provides the preceding method, wherein the HCN channel is HCN2.

This invention further provides the preceding method, wherein the HCN channel is HCN4.

This invention further provides the above-described method, wherein the compound comprises nucleic acids which encodes MiRP1 and a HCN channel. This invention provides the immediately preceding method, wherein the HCN channel is HCN1.

This invention also provides the preceding method, wherein the HCN channel is HCN2.

This invention further provides the preceding method, wherein the HCN channel is HCN4.

This invention further provides the above-described method, wherein the step of contacting is selected from the group consisting of topical application, systemic administration to the subject, injection, electroporation, liposome application, viral-mediated contact, contacting the cell with the nucleic acid, and coculturing the cell with the nucleic acid.

This invention provides the immediately preceding method, wherein the administration of contacting is selected from the group comprising topical administration, adenovirus infection, viral-mediated infection, liposome-mediated transfer, topical application to the cells of the subject, microinjection, and catheterization.

This invention further provides a method of inducing a current in the heart in a subject which comprises contacting a cell of the heart of a subject with a compound in a sufficient amount to induce a current in the cell of the heart of a subject, thereby inducing a current in the cell of the heart of the subject.

This invention further provides a method of increasing the heart rate in a subject which comprises contacting a cell of the heart of a subject with a compound in an amount sufficient to decrease the time constant of activation and deactivation of the cell of the heart, thereby increasing the heart rate in the subject.

This invention further provides a method of inducing a current in a cell which comprises contacting a cell with a compound in a sufficient amount to induce a current in the cell, thereby inducing a current in the cell.

This invention further provides a method of causing a contraction of a cell which comprises contacting the cell with a compound in an amount sufficient to induce a current required to cause a contraction of the cell, thereby causing a contraction of the cell.

This invention further provides a method of shortening the time required to activate and deactivate a cell which comprises contacting a cell with a compound in a sufficient amount to decrease the time constant of activation and deactivation of the cell, thereby shortening the time required to activate and deactivate the cell.

This invention further provides a method of changing the membrane potential of a cell which comprises contacting a cell with a compound in a sufficient amount to change the membrane potential of the cell, thereby changing the membrane potential of the cell.

This invention provides a method for the regulation of cardiac cells or specialized conducting fibers in the heart with HCN molecules, HCN 1, 2, or 4 isoforms of the pacemaker current, $I_f$, and or MiRP1 beta subunit, to produce a functioning site of impulse initiation that serves as the initiator of a heartbeat in settings where sinus node function is abnormal and or the sinus beat cannot activate the atria and or the ventricles.

As used herein, the term "cardiac cell of a heart" means a cell derived from a heart, either isolated or in culture.

As used herein, the term "a cardiac myocyte" means a myocyte derived from muscle or conductive tissue of a heart, either isolated or in culture and capable of initiating a current.

As used herein, the term "beating rate" means (1) the rate of a contraction or contractions over a given time period by a cell or (2) the rate of an electrical pulse or electrical pulses over a given time period by a cell.

As used herein, the term "membrane potential of the cell" means the transmembrane potential across the plasma membrane of a cell.

As used herein, the term "inducing a current" means causing a cell to produce an electrical current.

As used herein, the term "time required to activate and deactivate a cell" means the time period from activation of a cell the deactivation of the cell.

EXPERIMENTAL DETAILS EXAMPLE 1

HCN Over-Expression in Newborn and Adult Ventricular Myocytes: Distinct Effects on Gating and Excitability The following abbreviations are used herein: HCN—Hyperpolarization-activated Cyclic Nucleotide gated; minK—minimal K channel protein; MiRP1—minK-related peptide 1; $I_f$—Pacemaker current; mV—millivolts; cAMP—cyclic adenosine monophosphate; Ad—Adenovirus.

Introduction

Four members of the HCN gene family are currently known (13–15). Three of these (HCN1, HCN2 and HCN4) are present in the heart, but the relative message level of the three isoforms varies with region and age (16–18). Sinus node and Purkinje fibers, in which $I_f$ activates at less negative potentials, contain largely HCN1 and HCN4. Ventricle contains HCN2 and HCN4, with the ratio of mRNA of HCN2 relative to HCN4 being greater in the adult than newborn ventricle. This suggests that HCN2 is an inherently negatively activating isoform whose relative abundance determines the activation threshold in different regions of the heart or at different ages. However, heterologous expression studies do not support this simple explanation. While there is some variability between laboratories, when HCN2 and HCN4 have been expressed in mammalian cell lines activation voltages differed by less than 10 mV (18–20). Thus, the intrinsic characteristics of the specific HCN isoform expressed does not seem, by itself, to be a sufficient explanation for the diverse voltage dependence of the native $I_f$, either regionally in the adult heart or developmentally in the ventricle.

An alternative hypothesis is that the cellular environment in which a particular isoform is expressed influences its voltage dependence. The cellular environment could include the presence or absence of beta subunits, cytoskeletal elements, kinases, phosphatases or other factors. Because of these potential differences, HCN2 and/or HCN4 voltage dependence might differ when expressed in myocytes rather than in a heterologous expression system. For the same reason, one or both of these isoforms may be sensitive to the maturational state of the myocyte, exhibiting distinct voltage dependence when expressed in newborn as compared to adult ventricular cells. Here, data is presented to address these issues.

Material and Methods

Cell Isolation and Culture

Adult rats were anesthetized with ketamine-xylazine before cardiectomy, and neonatal rats decapitated, in accordance with the Institutional Animal Care and Use Committee protocols of Columbia University. For preparing cell cultures of newborn ventricles, a standard trypsin dissociation method was employed (21). The cells were preplated to reduce fibroblast proliferation, cultured initially in serum-containing medium (except when being transfected with plasmids as described below) and then switched to a serum free medium (SFM) after 24 hours. Action potential studies were conducted on 4 day old monolayer cultures plated directly onto fibronectin coated 9×22 mm glass coverslips. For voltage clamp experiments, 4–6 day old monolayer cultures were resuspended by brief (2–3 min) exposure to 0.25% trypsin, then the cells replated onto fibronectin-coated coverslips and studied within 2–8 hours.

Freshly isolated adult ventricle myocytes were prepared using the procedure described by Kuznetsov et al. (22). This entailed a Langendorff perfusion of collagenase, followed by trimming away of the atria. The remaining tissue was minced and dissociated in additional collagenase solution. The isolated myocytes were suspended in a serum free medium (ACCTI (23)) then plated on 9×22 mm glass coverslips at 0.5–1×10³ cells/mm². Two to three hours later, after the myocytes had adhered to the coverslips, the adenoviral infection procedure was begun (see below).

Expression of HCN Isoforms cDNAs encoding mouse HCN2 (mHCN2, GenBank AJ225122) or HCN4 (mHCN4, GenBank deposit in progress) were subcloned into the pCI mammalian Expression Vector (Promega, Madison, Wis.). The resulting plasmids (pCI-mHCN2 or pCI-mHCN4) were used for neonatal rat ventricular myocyte transfection, as indicated. A separate plasmid (pEGFP-C1; Clontech, Palo Alto, Calif.) expressing the gene of enhanced green fluorescent protein (GFP) as a visual marker for successful DNA transfer was included in all transfection experiments. For transfection, 2 μg pCI-mHCN and 1 μg pEGFP-C1 were first incubated in 200 μl SFM with 10 μl lipofectin (Gibco Life Technologies, Rockville, Md.) at room temperature for 45 minutes. The mixture was then added to a 35-mm petri dish containing ~10⁶ cells suspended in 0.8 ml SFM. After overnight incubation at 37° C. in a $CO_2$ incubator, the medium containing the plasmids and lipofectin was discarded and the dish was refilled with 2 ml fresh SFM. Patch clamp experiments were carried out on resuspended cells exhibiting detectable levels of GFP by fluorescence microscopy 3–5 days after transfection.

For increased expression efficiency, an adenoviral construct for mHCN2 was prepared. Gene delivery and transfer procedures followed previously published methods (24,25). A DNA fragment (between EcoRI and XbaI restriction sites) that included mHCN2 DNA downstream of the CMV promoter was obtained from plasmid pTR-mHCN2 (26) and subcloned into the shuttle vector pDC516 (AdMax™; Microbix Biosystems, Toronto, Canada). The resulting pDC516-mHCN2 shuttle plasmid was co-transfected with a 35.5 kb E1-deleted Ad genomic plasmid pBHGfrt E1, 3FLP (AdMax™) into E1-complementing HEK293 cells. The adenoviral construct AdHCN2 was subsequently harvested and CsCl purified.

For adult rat ventricular myocytes, AdHCN2 infection was carried out 2–3 hours after the isolated cells were plated onto coverslips. For neonatal cells, the infection was done on the monolayer culture 1–3 days after plating. In either case, the culture medium was removed from the dishes (35-mm) and the inoculum of 0.2–0.3 ml/dish was added containing AdHCN2. The value of m.o.i. (multiplicity of infection—the ratio of viral units to cells) was 15–100. The inoculum was dispersed over the cells every 20 min by gently "tilting" the dishes so that the cells were evenly exposed to the viral particles. The dishes were kept at 37° C. in a $CO_2$ incubator during the adsorption period of two hours, then the inoculum was discarded and the dishes were washed and refilled with the appropriate culture medium. The dishes remained in the incubator for 24–48 hours before electrophysiological experiments were conducted. In some experiments, an adenoviral construct for GFP (AdGFP) was employed.

Electrophysiologic Recording and Data Analysis

The whole-cell voltage clamp technique was employed to record native $I_f$ or expressed $I_{HCN2}$ or $I_{HCN4}$. Action potentials were recorded in current clamp mode, again using a whole cell patch electrode/Experiments were carried out on cells supervised at 35° C. Extracellular solution contained (mmol/L): NaCl, 140; NaOH, 2.3; $MgCl_2$, 1; KCl, 5.4; $CaCl_2$, 1.0; HEPES, 5; glucose, 10; pH 7.4. To record from myocytes expressing native currents ($I_f$), myocytes expressing HCN2 ($I_{HCN2}$) or HCN4 ($I_{HCN4}$), $[K^+]_o$ was increased to 10 mmol/L, and $MnCl_2$ (2 mmol/L) and $BaCl_2$ (4 mmol/L) added to the superfusate to eliminate calcium and inward rectifier ($I_{K1}$) currents. In some experiments CsCl (4 mmol/L) was used extracellularly to identify the pacemaker current as the Cs-sensitive current. The patch pipette solution included (mmol/L): aspartic acid, 130; KOH, 146; NaCl, 10; $CaCl_2$, 2; EGTA-KOH, 5; Mg-ATP, 2; HEPES-KOH, 10, pH 7.2. Where indicated, 10 μmol/L cAMP was included in the pipette solution. A fast solution changing apparatus expedited the experimental protocols. The pipette resistance was typically 1–3 M. An Axopatch-200B amplifier and pClampS software (Axon Instruments) were used for acquisition and data analysis. The pacemaker current ($I_f$, $I_{HCN2}$ or $I_{HCN4}$) was defined as the time-dependent component taken at the end of a hyperpolarizing step to voltages in the range of −35 to −145 mV, while the holding potential was −35 mV unless otherwise indicated. For $I_f$ and $I_{HCN2}$ measurements, the hyperpolarizing test pulses were 3 or 6 sec long throughout the voltage range. To accurately record steady-state currents for the more slowly activating $I_{HCN4}$, the test voltages varied in length from 6 sec at −125 mV to as long as 60 sec at −55 mV. When recording tail currents, the test pulses were followed by an 8-sec voltage step to −125 mV. In all pacemaker current protocols, each episode ended with a pulse to −5 mV for 0.5 sec to insure full deactivation.

Figure 2A:
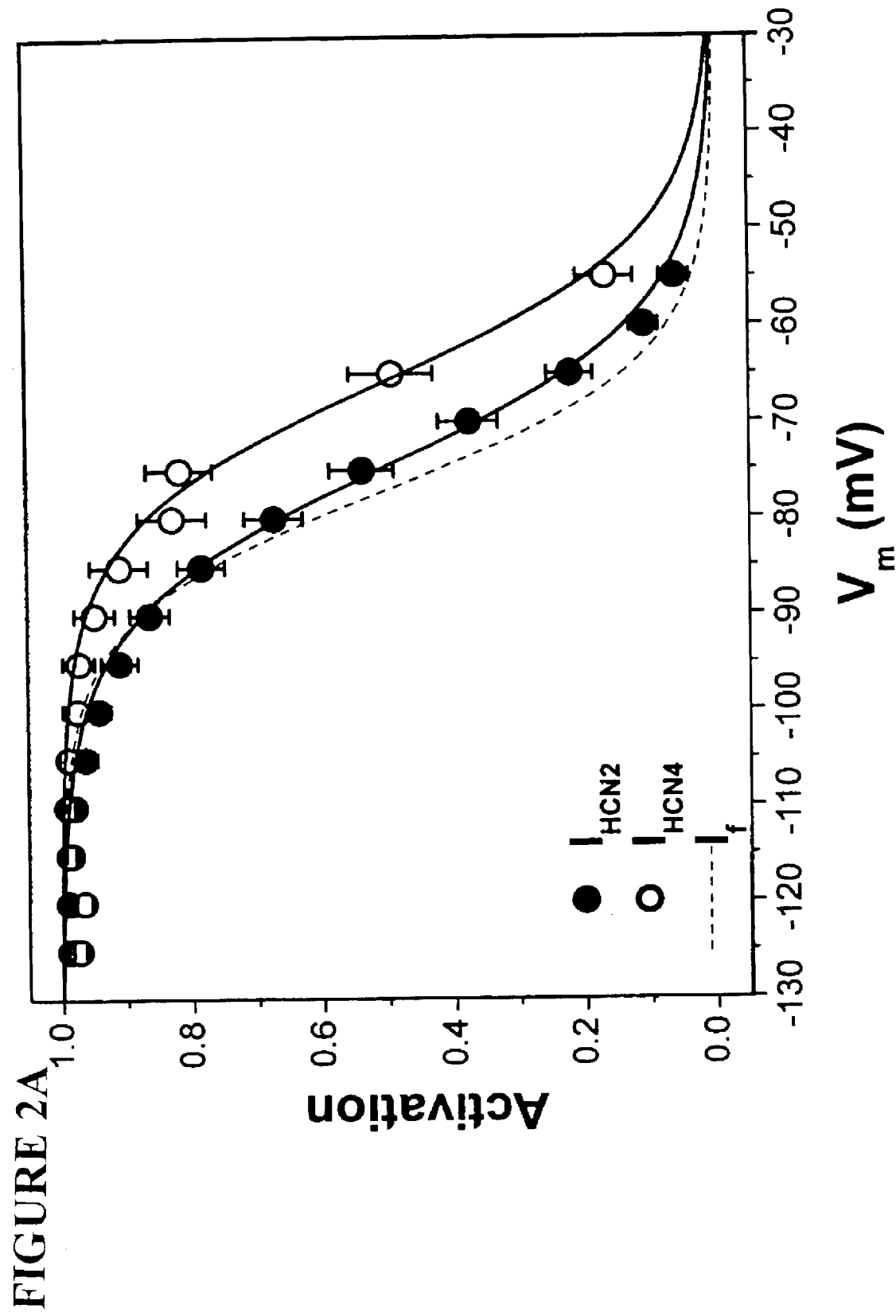
FIGS. 2A–B: activation-voltage relation and kinetics of expressed HCN2 and HCN4 in neonatal ventricle. A: I-V curves converted to activation relation using a Boltzmann relation. Activation relation for native current (dashed line) is taken from (28). B: time constant of current activation for native $I_f$ and for expressed $I_{HCN2}$ and $I_{HCN4}$.

The activation relation of the native or expressed current can be determined from the steady-state I-V relation. In this case, the reversal potential ($V_f$) was separately determined from the fully activated I-V relation (27) and used to generate the activation relation ($y=I/(g_{max}*(V-V_f))$), where $g_{max}$ is the maximal conductance). This method was used in the initial studies of expression with HCN2 or HCN4 plasmid in neonatal rat ventricular cells (FIG. 2A). Subsequent studies of $I_f$ or $I_{HCN2}$ employed tail current measurements. Tail current, after being plotted against the test voltage, gave the maximum conductance and activation-voltage relation. This relation was normalized by the maximum conductance and fitted with the Boltzmann function ($y=1/(1+\exp((V-V_{1/2})/K))$) to determine the voltage of half maximum activation ($V_{1/2}$) and slope factor (K). Tail currents were measured at a negative voltage (−125 mV) to avoid contamination by transient outward and other currents at less negative voltages.

The kinetics of activation were determined by a single exponential fit to the early time course of the current activated by hyperpolarizing pulses. Both the initial delay and any late slow activation were ignored. The kinetics of deactivation were determined by a single exponential fit of the time course of the current trace at each test voltage after maximal activation by a conditioning pulse to −125 mV. For both activation and deactivation, the length of the current trace being fit was at least three times as long as the measured time constant to insure accuracy.

Data Analysis and Statistics

All data are presented as mean±S.E.M. Statistical significance was examined by f-test for paired and ANOVA for multiple comparisons, and determined at $P<0.05$.

Results

Comparison of Neonatal Ventricular Myocytes Expressing HCN2 and HCN4

Figure 1B:
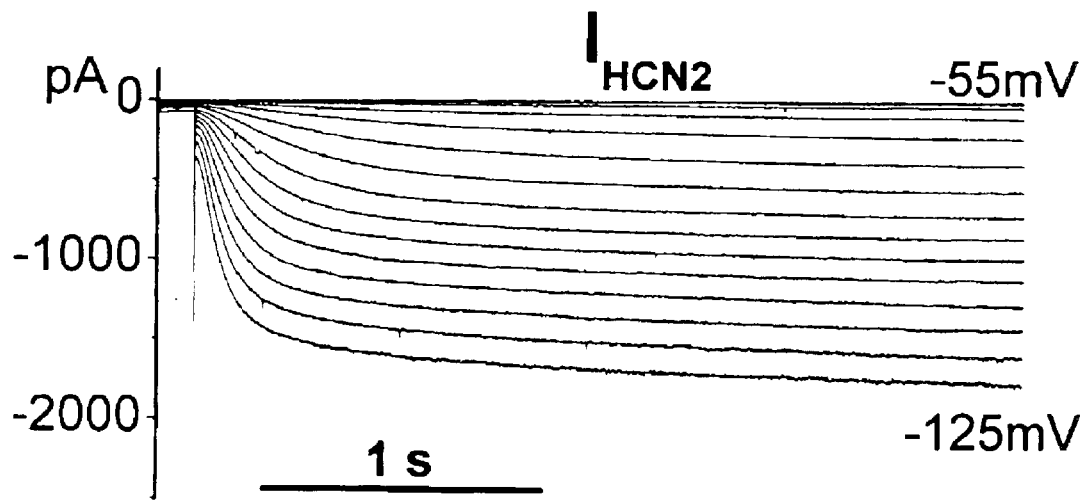
Figure 1C:
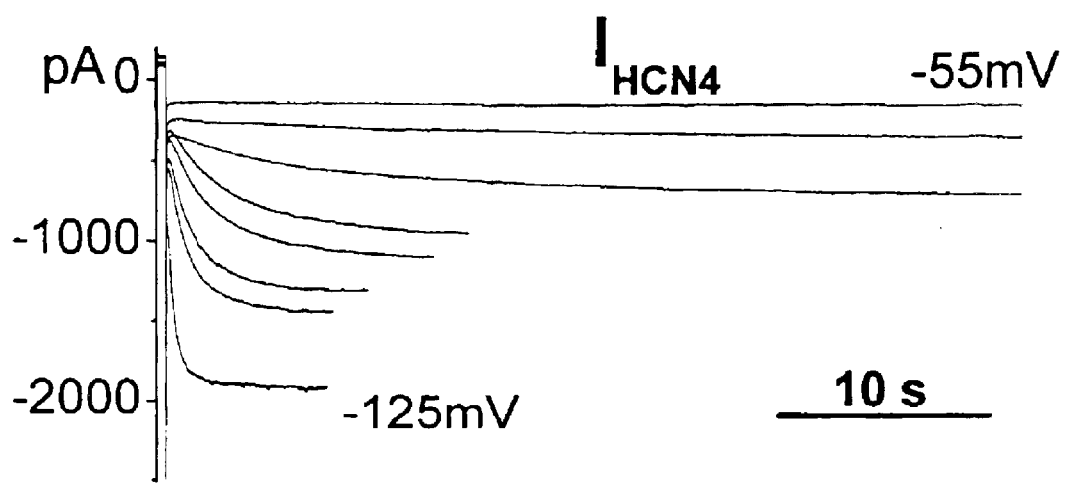

It has previously been reported that neonatal rat ventricle cells in culture exhibit a small $I_f$ that activates with a threshold voltage around −70 mV (8,10). FIG. 1A provides a representative family of current traces of the native $I_f$ in a neonatal rat ventricle cell in culture. A time-dependent inward current component is apparent for voltage steps of −65 mV or more negative. Studies of message levels by RNase protection assay have indicated that both HCN2 and HCN4 are present in the newborn ventricle, with relative message levels of about 5:1 (16). Therefore, each of these isoforms were expressed separately in the neonatal ventricle cultures. As described in *Material and Methods*, a lipofectin transfection method was employed and the HCN plasmids were co-transfected with pEGFP-C1 to aid in the identification of expressing cells. Expression efficiency was less than 5%, based on the number of visually detected fluorescent cells. More than 90% of fluorescent cells possessed an $I_f$-like current at least 10 times greater in magnitude than the native current. FIGS. 1B–C illustrates representative expressed current traces from myocytes transfected with HCN2 and HCN4, respectively. The current magnitude is such as to clearly distinguish the expressed current from the native current. Further, the slower kinetics of the expressed HCN4, compared to HCN2, is apparent (note different time scale in FIG. 1C). Slower HCN4 kinetics also have been reported in heterologous expression studies.

Figure 2B:
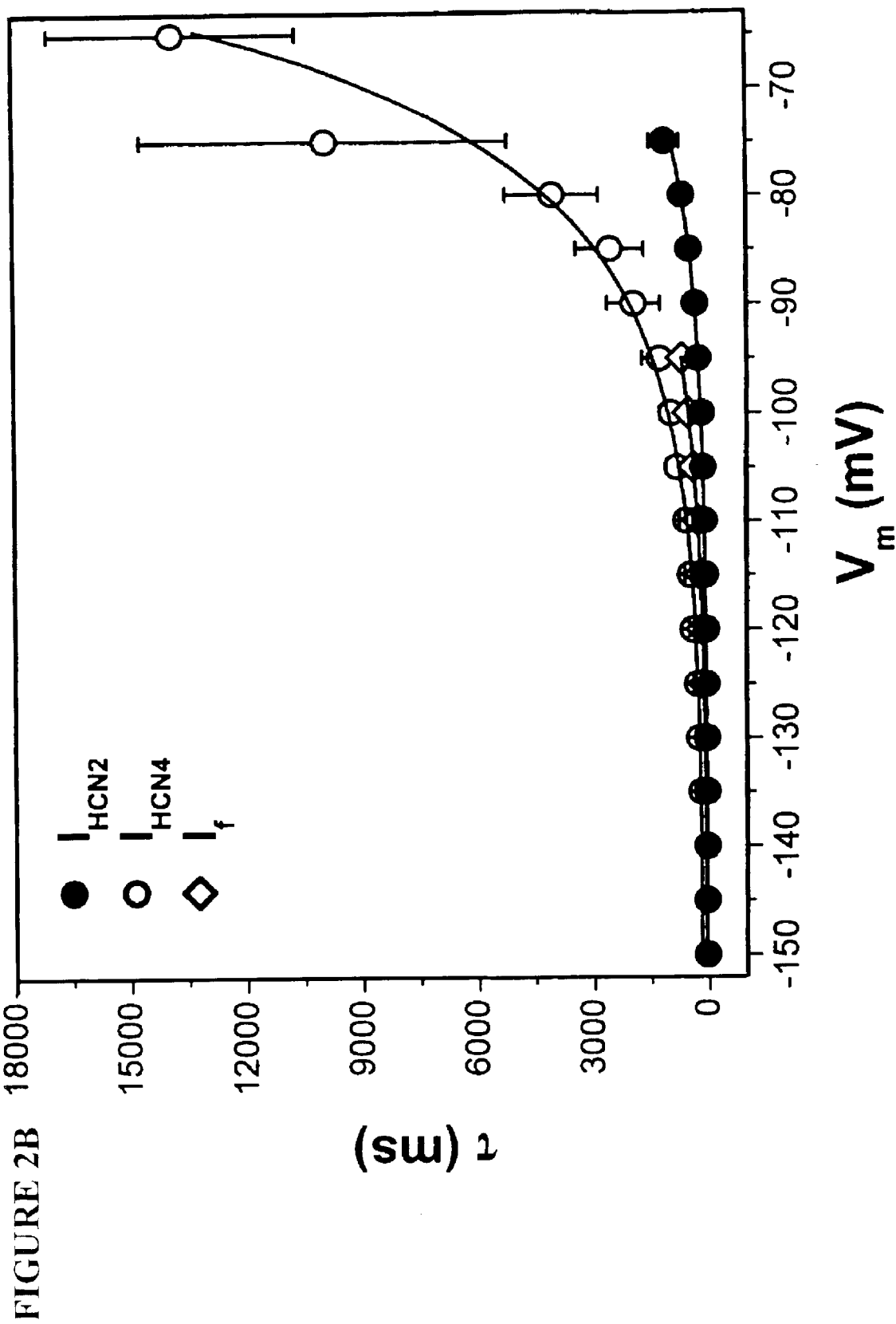

Current records such as those illustrated in FIG. 1 were used to determine the quasi steady-state I-V relation. For the native current and for expressed HCN2, 3-sec voltage steps were sufficient to approximate steady-state at most of the test voltages, although the current did not achieve steady-state at the less negative steps. Significantly longer pulses were required for adequate analysis of HCN4. Reversal potential in each case was separately determined (see *Material and Methods*), and used to convert the I-V relation to the corresponding activation relation of the native and expressed current. The average activation relations for native current (taken from (28)) and for expressed currents are shown in FIG. 2A. The experiments were conducted on 4–6 day old cultures that had been transfected the same day as cells were dissociated. Neonatal myocytes expressing HCN2 exhibited currents that activated at more negative voltages than those expressing HCN4, and this difference was statistically significant ($V_{1/2}$ of $-74.8\pm1.4$, n=17, and $-66.3\pm2.0$ mV, n=14, respectively; P=0.001). Slope factors (K) did not differ ($7.7\pm0.7$ and $6.7\pm0.7$ mV; P=0.348). The 8.5 mV difference in midpoint of activation of HCN2 and HCN4, while statistically different, is considerably less than the 40 mV difference (based on threshold measurements) between adult and neonatal ventricle. This suggests that, while a developmental increase in the HCN2/HCN4 ratio might contribute to the age-dependent negative shift in activation of $I_f$, it cannot fully explain the shift. FIG. 2B compares the activation kinetics of the currents recorded from neonatal ventricular myocytes expressing HCN2 (n=6–9) and HCN4 (n=4–5). For most voltages, HCN4 activation kinetics are markedly slower than those of HCN2. Since HCN4 activates at less negative voltages than HCN2, this cannot be explained by a shift in the voltage dependence of activation. Rather, it represents a basic difference in the kinetics of the two isoforms, as has also been reported in heterologous expression experiments (18, 20). The native $I_f$ (n=8) demonstrates activation kinetics intermediate between those of HCN2 and HCN4, but the small magnitude of the native current made it impractical to obtain reliable kinetic data at less negative voltages, where the behavior of the two expressed isoforms more markedly diverge.

Comparison of Neonatal and Adult Ventricular Myocytes Expressing HCN2

Figure 3D:
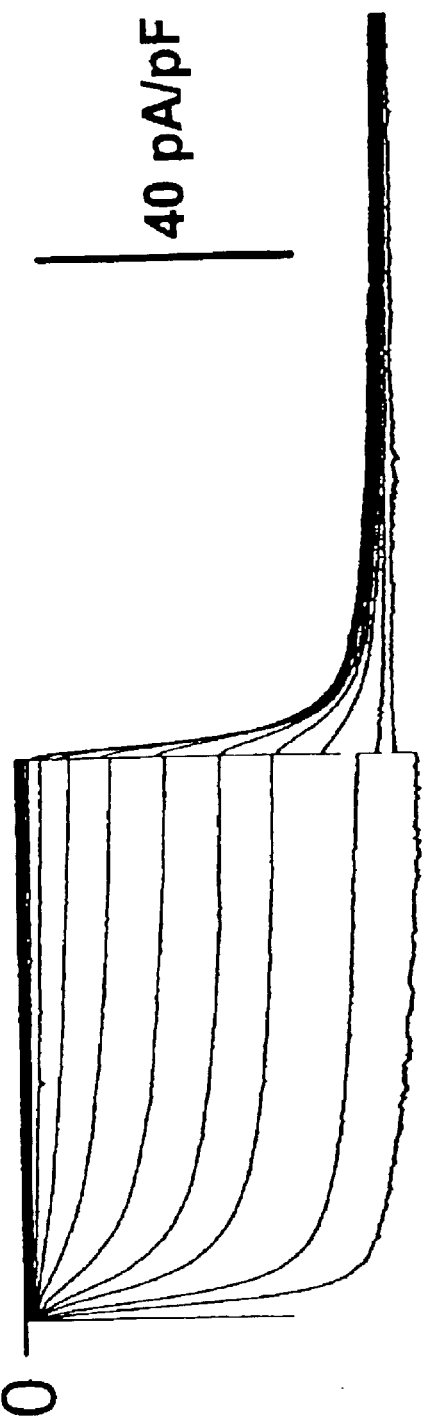
Figure 3D:
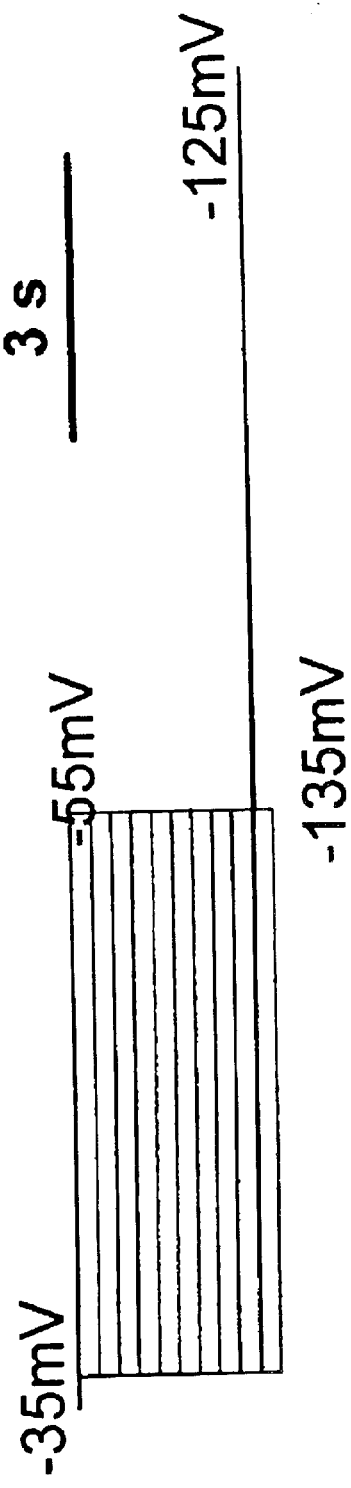

Since the preceding experiments suggested that an HCN4/HCN2 isoform switch was not likely to fully account for the differences in native $I_f$ between neonatal and adult ventricle, what was next sought was to compare the characteristics of HCN2 (the major ventricular HCN isoform, at the message level, at both ages (16)) when expressed in adult versus neonatal ventricular myocytes. This required maintaining adult ventricle cells in culture for 48 hours. An earlier report indicated that longer culture conditions could result in a marked positive shift in the voltage dependence of activation of native current (9). Therefore what was first compared was native current in acutely dissociated cells with that in cells maintained in culture in serum free medium for 2 days. A voltage clamp protocol that allowed direct construction of the activation relation without the need for a separate determination of the reversal potential, was employed. After a hyperpolarizing step to various test voltages, a second step to $-125$ mV generated a tail current, the amplitude of which was employed to determine the activation relation. FIGS. 3A–B provides representative current traces from acutely dissociated and cultured adult rat ventricle cells. In both cases, the cells were rod-shaped and quiescent and, as seen in the figure, in both cases the threshold voltage (i.e. first voltage step where a time dependent current is apparent) is more negative than was seen for the native current in the neonate (FIG. 1A). The lipofectin transfection method, with its low efficiency, was inadequate for studies of HCN expression in adult myocytes. Therefore, an adenoviral construct (AdHCN2, see *Material and Methods*) that contained the mouse HCN2 sequence was prepared. Treatment of the adult cells with this adenoviral construct resulted in expression of high current levels (FIG. 3C, note different scale). In adult ventricular myocytes expressing HCN2, the recorded current activated with a more negative threshold than that previously observed in neonatal cells (FIG. 1B).

Figure 4A:
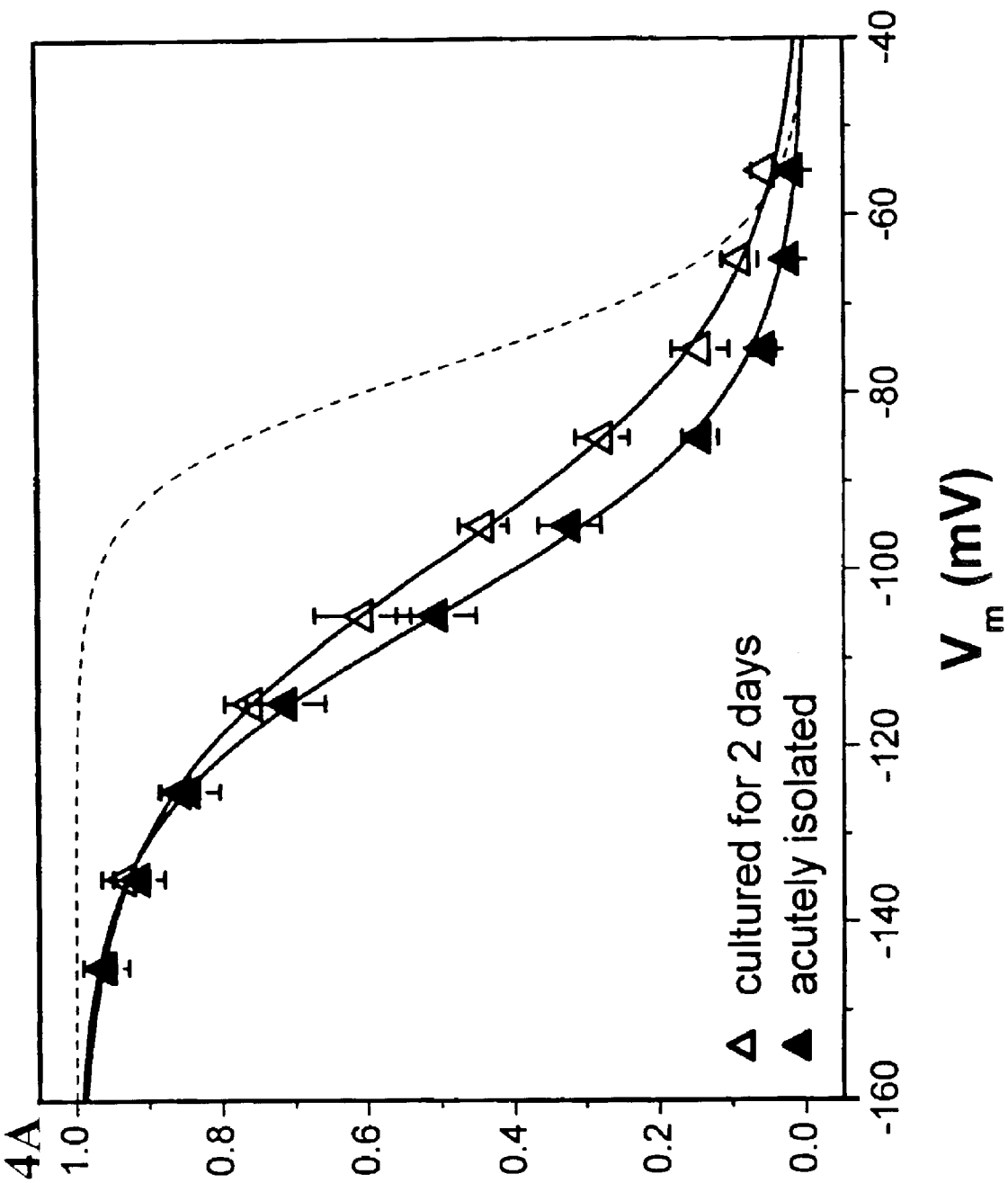
FIGS. 4A–B: activation relation and kinetics of native $I_f$ in adult myocytes. A: activation relation for $I_f$ in acutely dissociated and cultured adult ventricular myocytes. B: time constant of current activation for native $I_f$ in acutely isolated and cultured adult ventricular myocytes. Neonatal data from FIG. 2 is superimposed as dashed line for comparison.
Figure 4B:
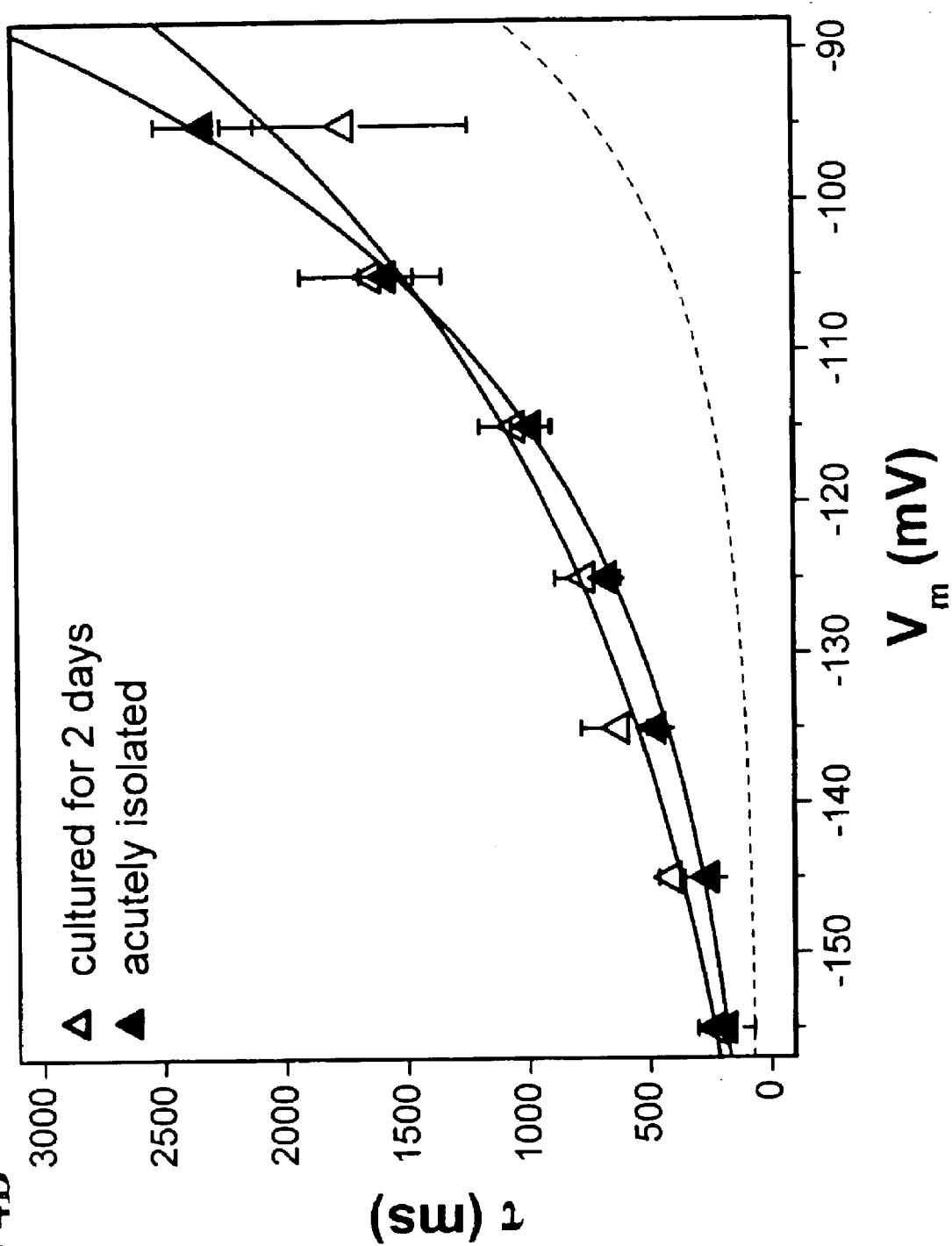

FIGS. 4A–B compares the activation relation and kinetics of native $I_f$ in acutely dissociated and cultured adult ventricle cells. A 2-day culture period resulted in no significant difference in $V_{1/2}$, although the trend was toward a less negative midpoint after culture ($-105.3\pm2.6$, n=12, vs. $-98.7\pm1.8$ mV, n=7, in acutely isolated vs. cultured cells; P=0.092); neither was there a significant difference in slope factor ($10.9\pm1.2$ vs. $14.4\pm1.9$ mV). Activation kinetics also did not differ between acutely isolated and cultured adult ventricle. The neonatal data from FIG. 2 are superimposed (dashed lines) to illustrate the neonatal/adult difference in voltage dependence and kinetics of activation of the native $I_f$. Thus, short-term culture does not significantly alter $I_f$; any trend in voltage dependence is modest compared to the effect of development. The neonatal/adult comparison confirms the earlier developmental study that reported an age-dependent difference in voltage dependence of activation (8).

Figure 5A:
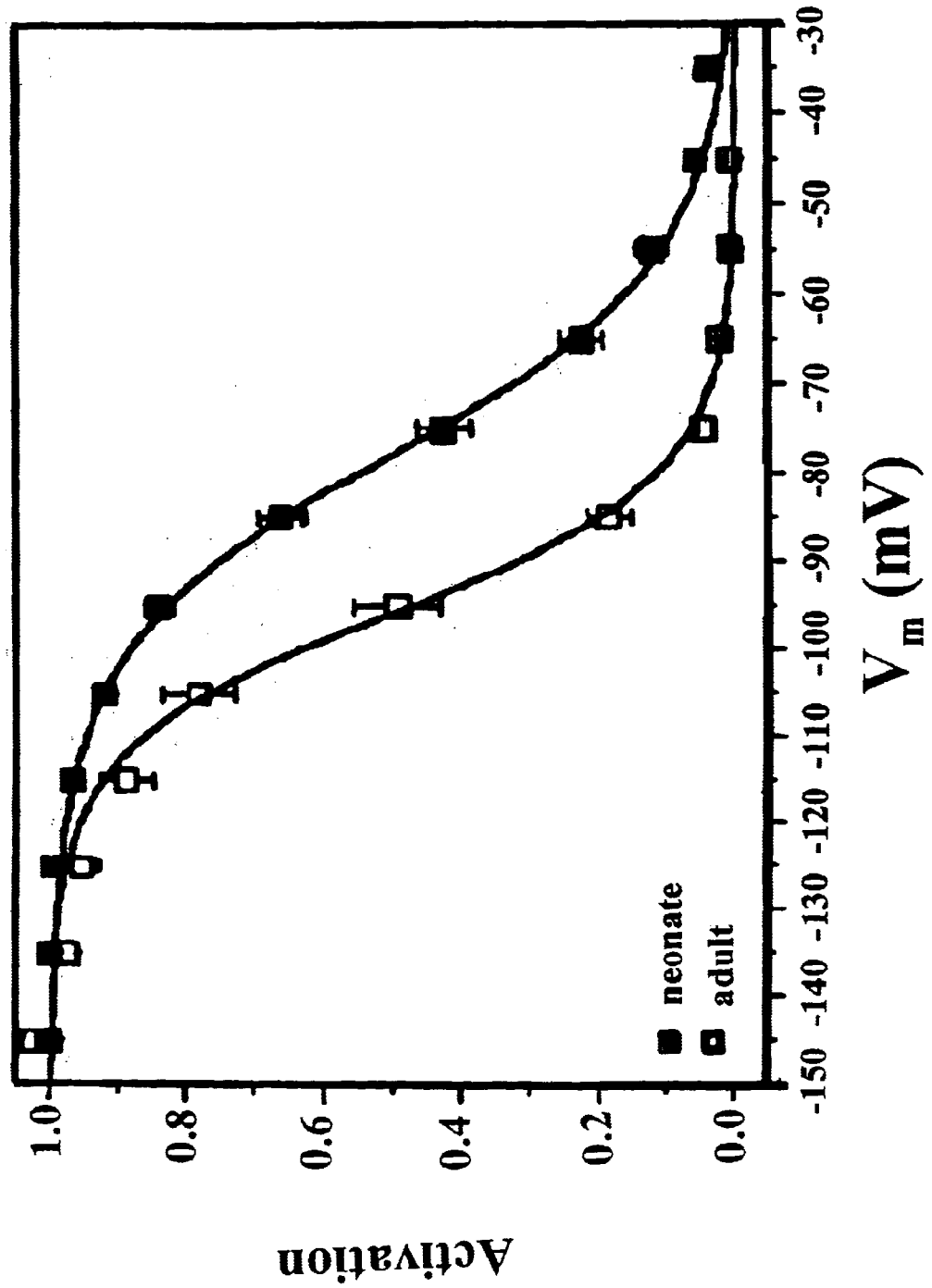
FIGS. 5A–B: activation relation and kinetics of $I_{HCN2}$ expressed with AdHCN2 in neonatal and adult ventricle. A: activation relations for neonatal and adult ventricle cultures as measured by tail currents. B: time constant of activation (squares) and deactivation (circles) for neonatal and adult myocytes. Lines are generated by a best fit to the equation.
Figure 5B:
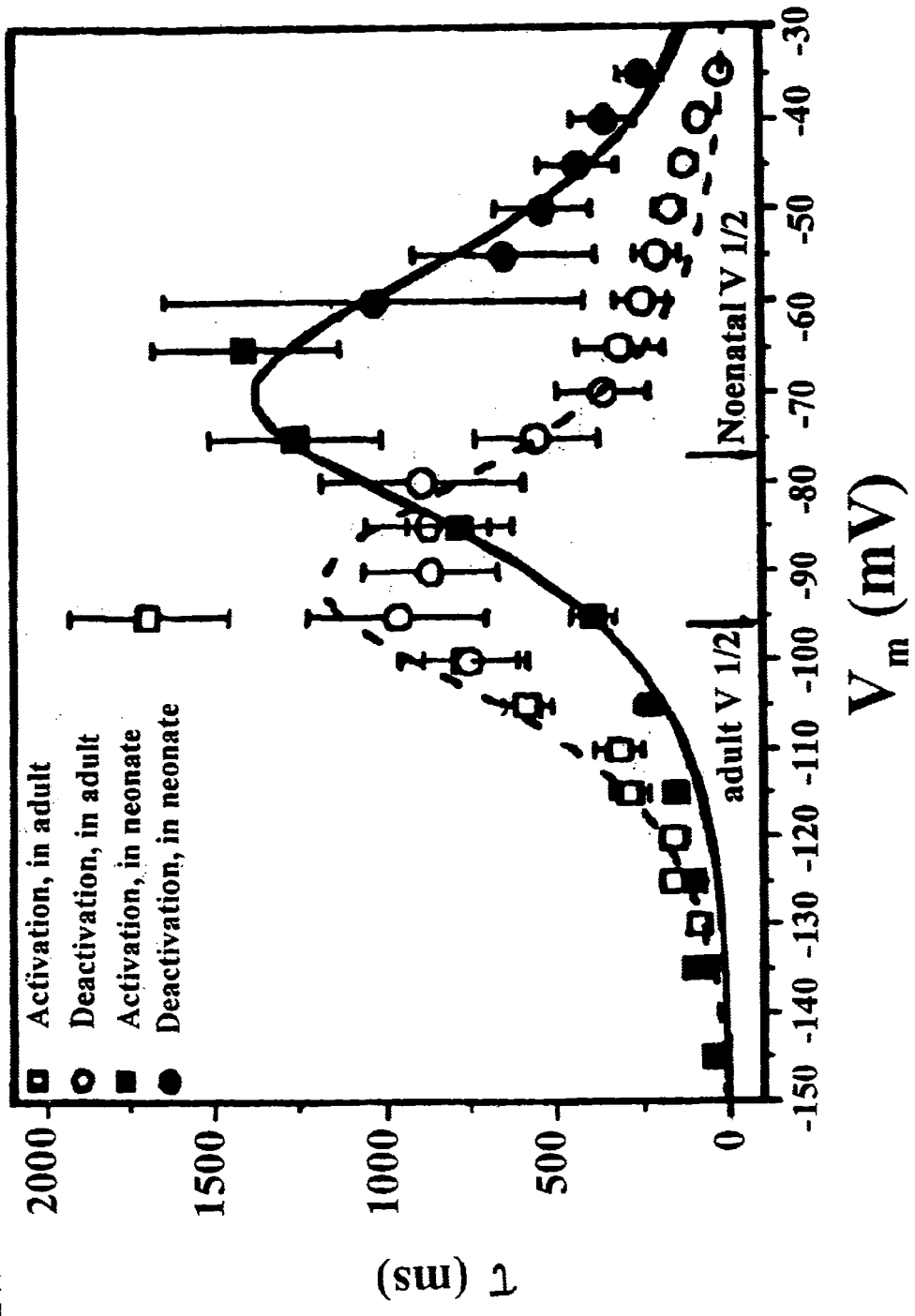

To compare the characteristics of HCN2 in neonatal and adult ventricular myocytes, the adenoviral construct with both preparations was used. The neonatal data are comparable to the earlier results using the lipofectin method (FIG. 2). FIG. 5A illustrates the average activation relations, from tail current measurements, obtained from myocytes expressing HCN2 in the two culture preparations. It is evident that, when the same protein is expressed in the neonatal and adult myocyte preparations, the resultant current activates at significantly more negative voltages in the adult cells. $V_{1/2}$ values for HCN2 expressed in neonatal and adult myocytes were $-77.6\pm1.6$ (n=24) and $-95.9\pm1.9$ mV (n=13), respectively (P<0.001). In addition, the slope factor (K) also differed significantly ($9.8\pm0.6$ vs. $6.5\pm0.5$ mV, P<0.001), reflecting a more shallow voltage dependence in the neonate. FIG. 5B provides data on the voltage dependence of activation/deactivation kinetics for the expressed HCN2. The data were well fit by a standard kinetic model (see legend), and exhibit little difference in the maximal value of activation time constant between the two cultures. However, the voltage dependence of the relation is shifted negative in the adult by an amount (21 mV) that is comparable to the shift in the activation relation (18 mV). Moreover, the relative peaks of the kinetic relations in the two culture preparations are consistent with the previously determined $V_{1/2}$ values (arrows, FIG. 5B). Thus, the difference in the voltage dependence of activation kinetics of HCN2, when expressed in neonatal and adult myocytes, appears related to the voltage dependence of the steady-state activation relation.

Possible Basis for Difference Between Neonatal and Adult Myocytes Expressing HCN2

Figure 6:
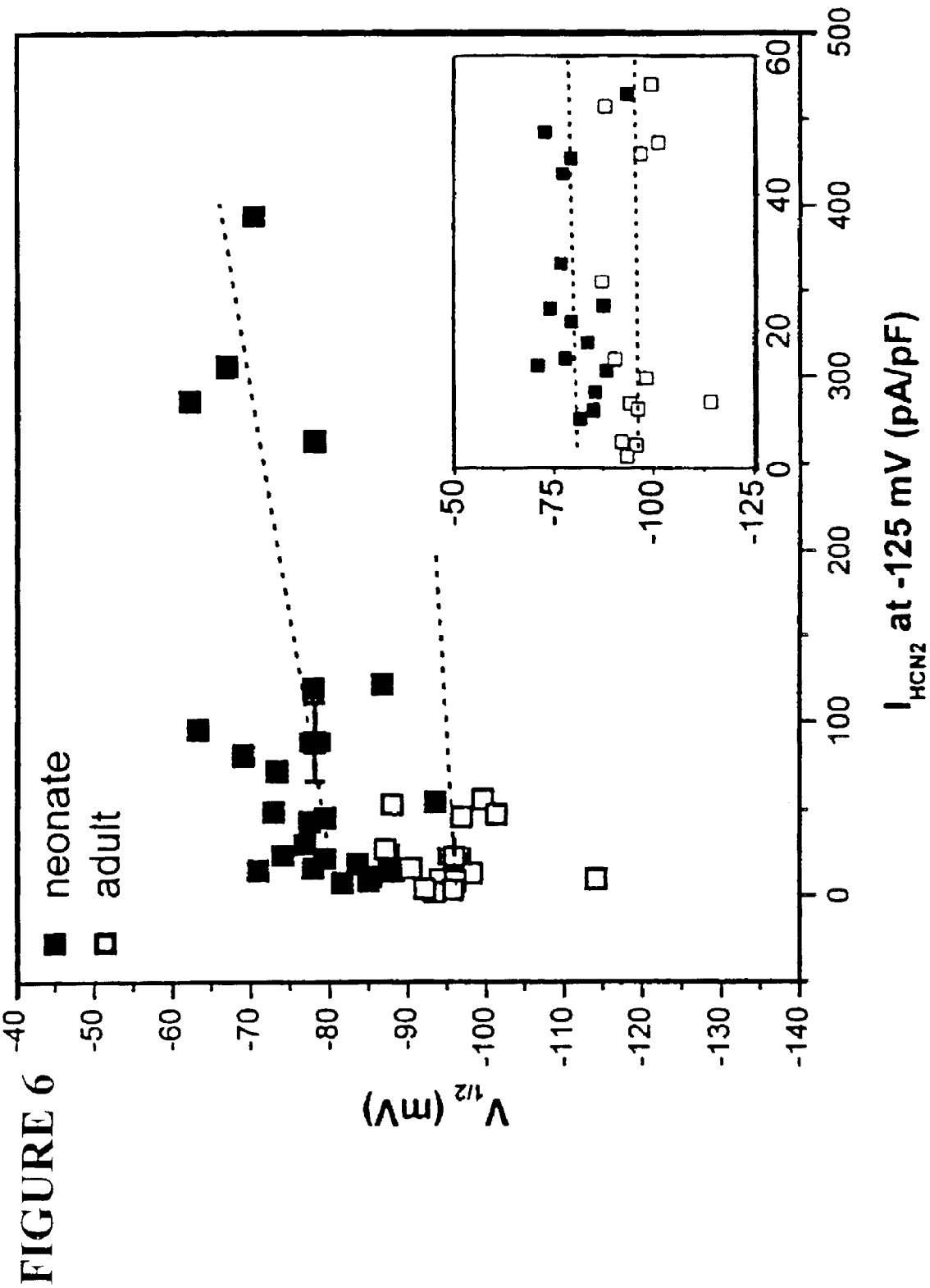
FIG. 6: regression relation for $V_{1/2}$ of Boltzmann relation as a function of expressed HCN2 current density in neonatal and adult myocytes. Here cultures were infected with AdHCN2. Lines are calculated linear regressions. The vertical and horizontal error bars represent S.E.M. of $V_{1/2}$ and $I_{HCN2}$, respectively. Inset shows expanded time scale for current densities <60 pA/pF.

In heterologous expression of other currents, the biophysical characteristics of the expressed currents can sometimes depend on the current density achieved (29–32). To determine $I_f$ the difference in $V_{1/2}$ of HCN2 between neonatal and adult was a result of this type of phenomenon, a linear regression analysis of the data was conducted(FIG. 6). The results indicate that, while there is some correlation of $V_{1/2}$ with current density in the newborn, differences in expression level cannot explain the difference in HCN2 voltage dependence between neonatal and adult myocytes. The neonatal myocytes exhibited a wide range of current density for the expressed current, with a correlation coefficient for $V_{1/2}$ of 0.51 (P=0.01); current density was less variable in the adult, with no correlation with activation midpoint (correlation coefficient 0.043, P=0.88). For current densities common to both preparations (i.e. <60 pA/pF, FIG. 6 inset) the expressed current in the neonatal myocytes demonstrated a significantly less negative $V_{1/2}$ than in the adult myocytes (P<0.001).

Figure 7:
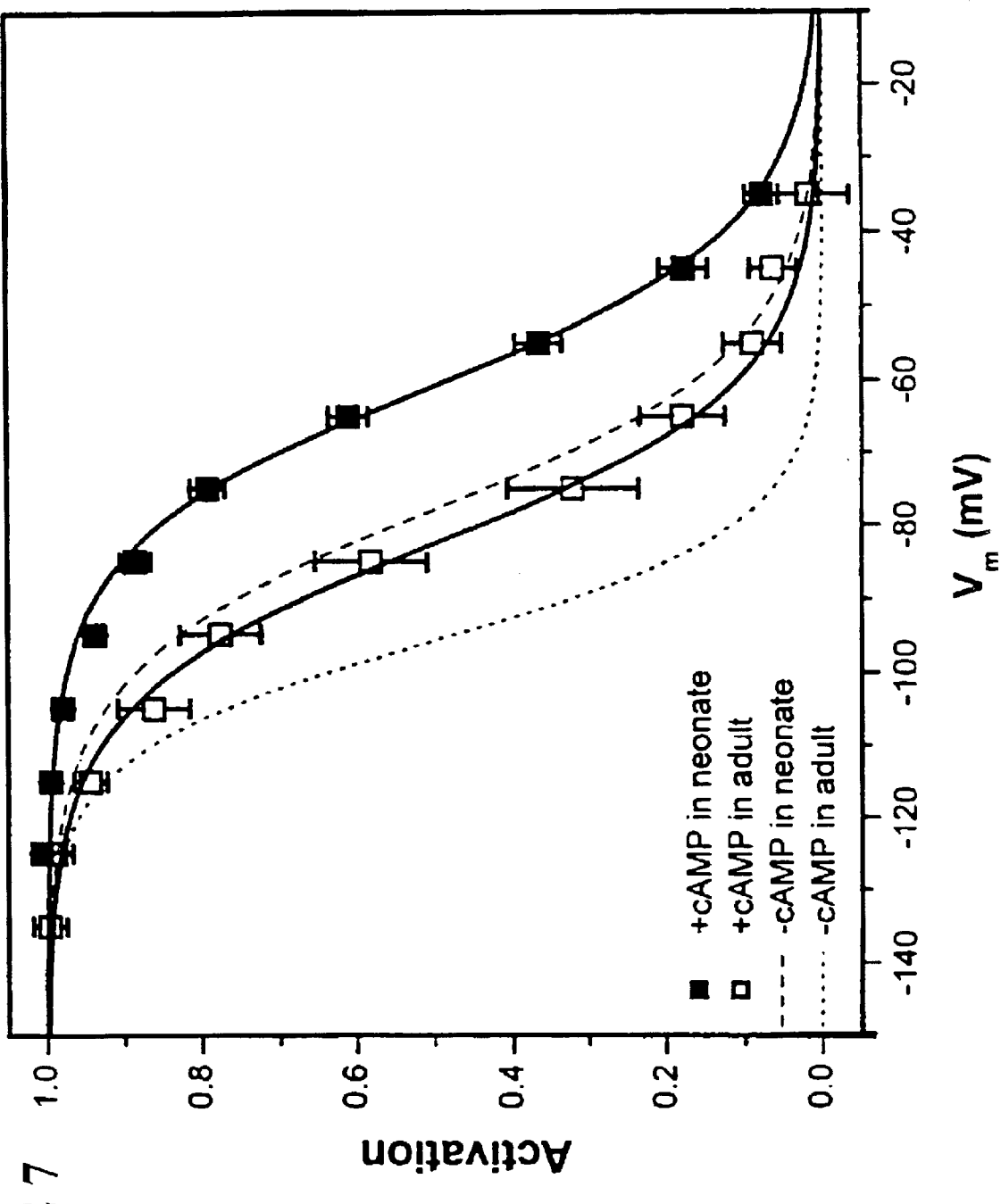
FIG. 7: effect of intracellular cAMP on activation relation of expressed HCN2 current in neonate and adult myocytes. Earlier data with control pipette solution (FIG. 5A) are shown as dashed (neonate) and dotted (adult) lines.

It is well known that both the native $I_f$ and the expressed current respond to cAMP by a phosphorylation independent shift in the voltage dependence of activation (33, 34), although phosphorylation-dependent mechanisms also have been reported (35–37). It is possible that the observed difference in activation of HCN2 in neonatal and adult myocytes simply reflected a different basal cAMP level within the two cells preparations was considered. To test this, the experiments measuring the activation relation of the expressed current with AdHCN2 in neonatal and adult cells were repeated, but this time the experiments included 10 μmol/L cAMP in the pipette solution to achieve a maximal positive shift of the current and eliminate any differences in intracellular cAMP levels. As seen in FIG. 7, the expressed current shifted positive by a comparable amount in both the neonatal and adult preparations (data in the absence of cAMP in the pipette are represented by the dashed and dotted lines), and the large difference in $V_{1/2}$ values persisted. Thus, the age-dependent difference in the voltage dependence of activation of HCN2 does not arise from a difference in basal cAMP level between the two preparations.

Functional Effect of Overexpression of HCN2

Figure 8A:
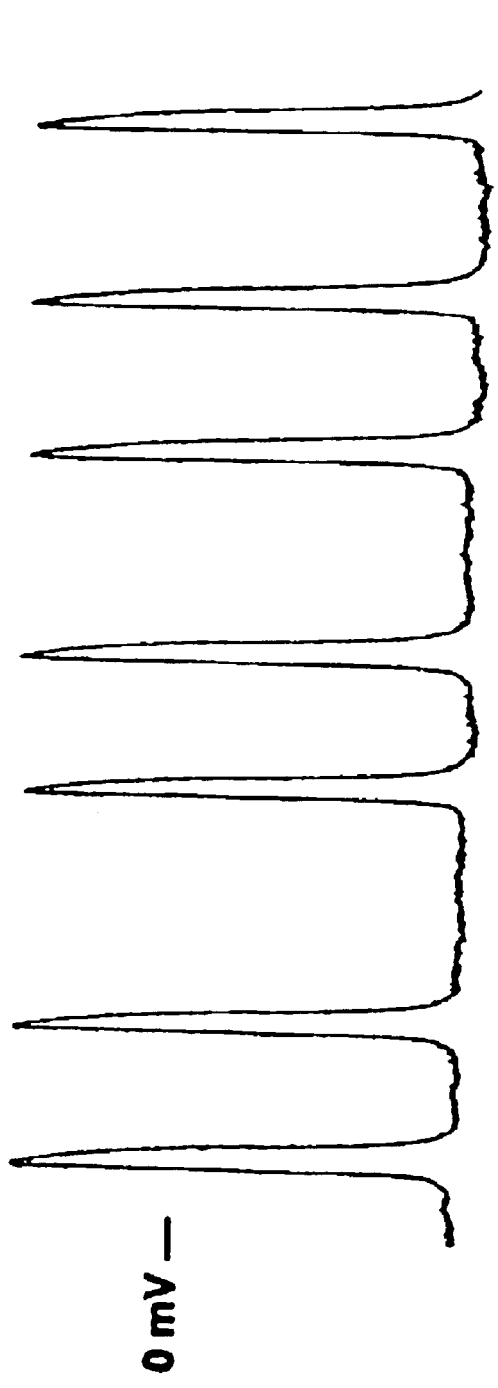
FIGS. 8A–C: show the effect of HCN2 overexpression on spontaneous activity of neonatal ventricle culture. Monolayer culture was infected with AdHCN2 or AdGFP and spontaneous action potentials subsequently recorded with whole-cell patch electrodes. A: spontaneous action potentials from a control monolayer culture. B: spontaneous action potentials from an AdHCN2 infected monolayer culture. C: summary data comparing control, AdHCN2 infected and AdGFP infected cultures with respect to spontaneous rate, slope of phase 4 depolarization and maximum diastolic potential (MDP). Asterisk indicates significant difference relative to control culture; n values for control were 16–17, for AdHCN2 infected were 12–16 and for AdGFP infected were 6.
Figure 8B:
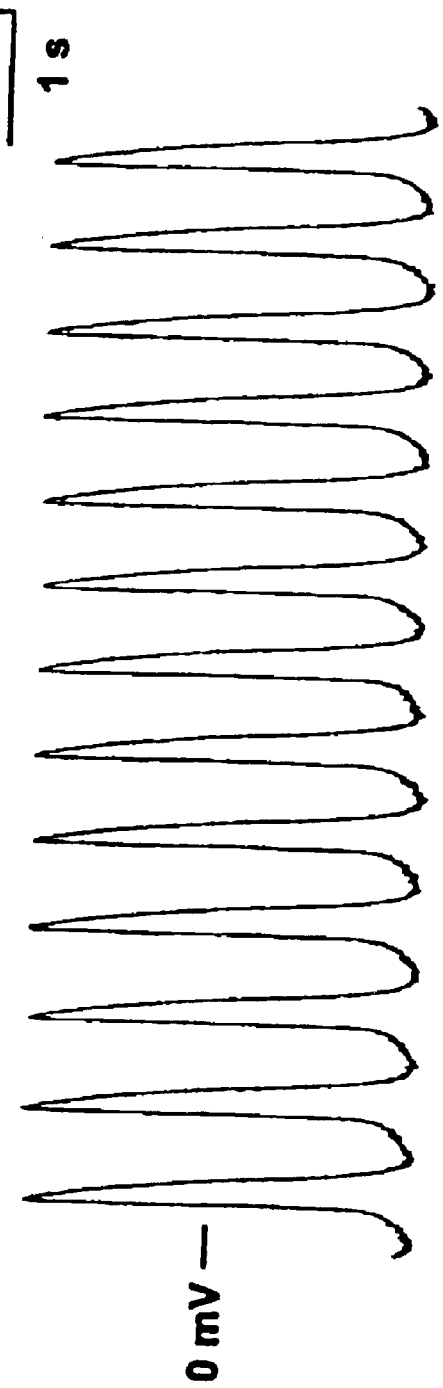
Figure 8C:
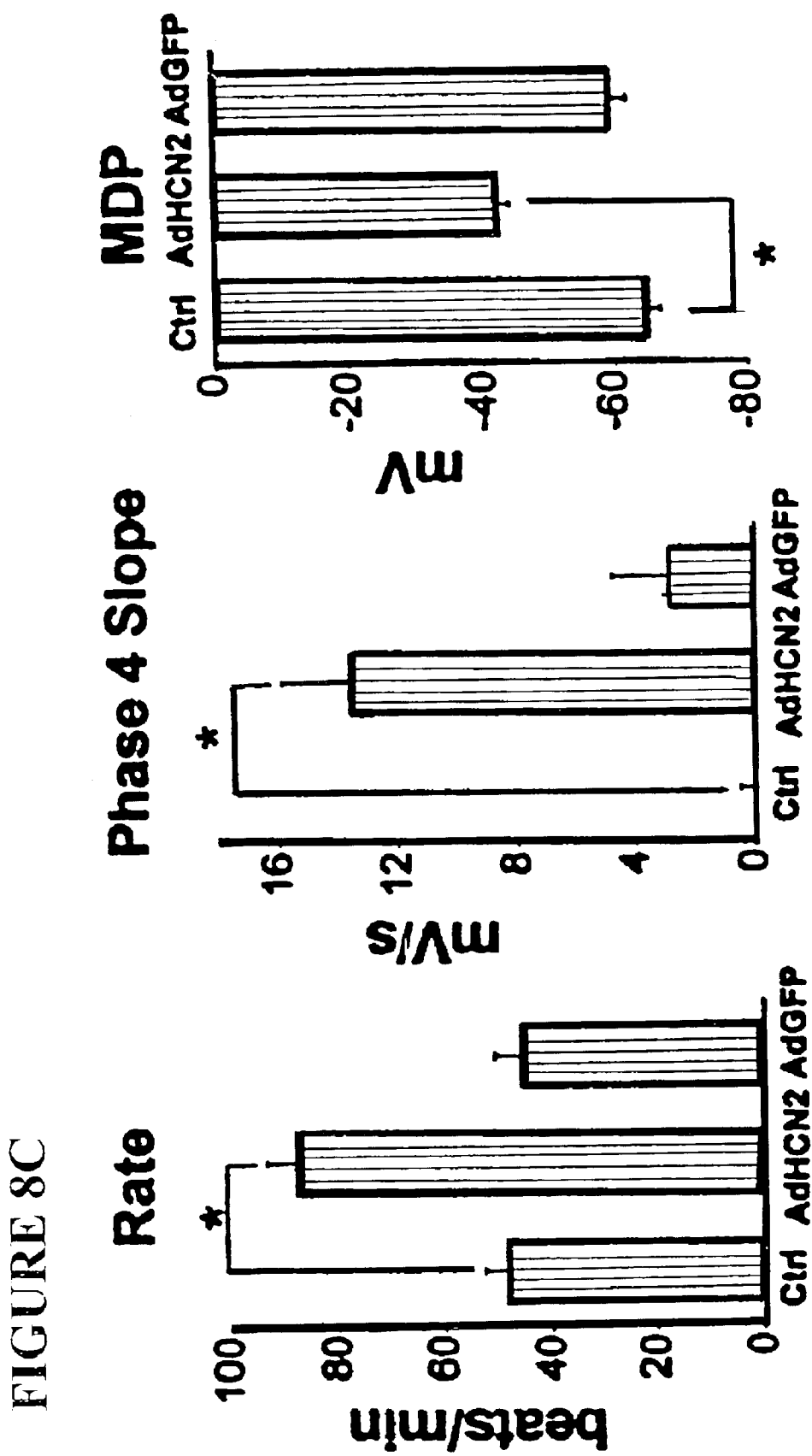

The adenoviral construct of HCN2 resulted in expression of a large current in the majority of cells (at least 90% of cells patch clamped). Given the relatively positive activation of the expressed current in the neonatal cells, placing it within the physiologic range of voltages, it was next determined if overexpression of HCN2 resulted in a change in spontaneous rate of these cultures. These experiments were conducted using monolayer cultures of synchronously beating cells, with a whole cell patch electrode recording from one cell of the contiguous monolayer. The control (non-infected) cultures beat spontaneously, with a mean rate of 48.4±4.4 beats per min (bpm, n=17). There was little or no diastolic depolarization between action potentials and the cycle length tended to vary from beat to beat (FIG. 8A). The maximum diastolic potential (MDP) was −65.2±1.8 mV (n=17). In contrast, the cultures infected with AdHCN2 exhibited a more regular and faster rhythm (FIG. 8B), with mean rate of 88.0±5.4 bpm (n=16). Further, these cultures exhibited a marked diastolic depolarization and a less negative MDP (FIG. 8C). The differences in frequency, phase 4 slope, and MDP were statistically significant (P<0.05). Cultures infected with AdGFP (frequency: 45.8±4.7 bpm; MDP: −59.5±2.4 mV; n=6) did not differ from uninfected control cultures, but did differ significantly from AdHCN2 infected cells.

Figure 9A:
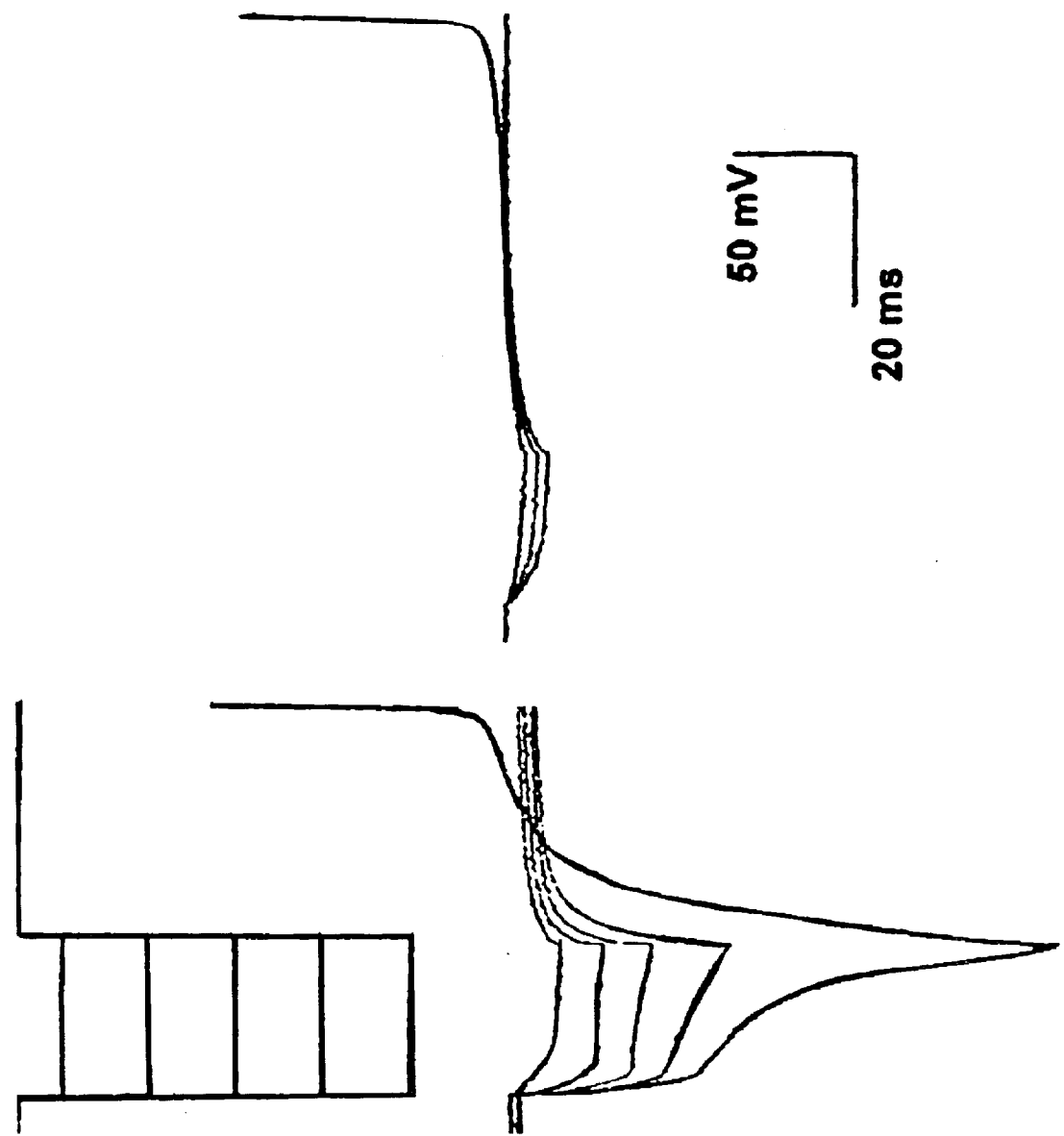
FIGS. 9A–B: effect of HCN2 overexpression in adult ventricular myocytes. A: representative anode break excitation tracings from a control myocyte (left, including stimulus time course) and an AdCN2 infected myocyte (right). Resting potential in the two examples is −66 and −60 mV, respectively. Only selected traces are shown for clarity. B: graph of relation between maximal negative potential achieved during anodal stimulation as a function of $I_f$ or $I_{HCN2}$ current density (measured at the end of a 2-sec step to −125 mV). Inset shows current density range of 0–1.2 pA/pF on an expanded time base, with calculated linear regression as solid line.
Figure 9B:
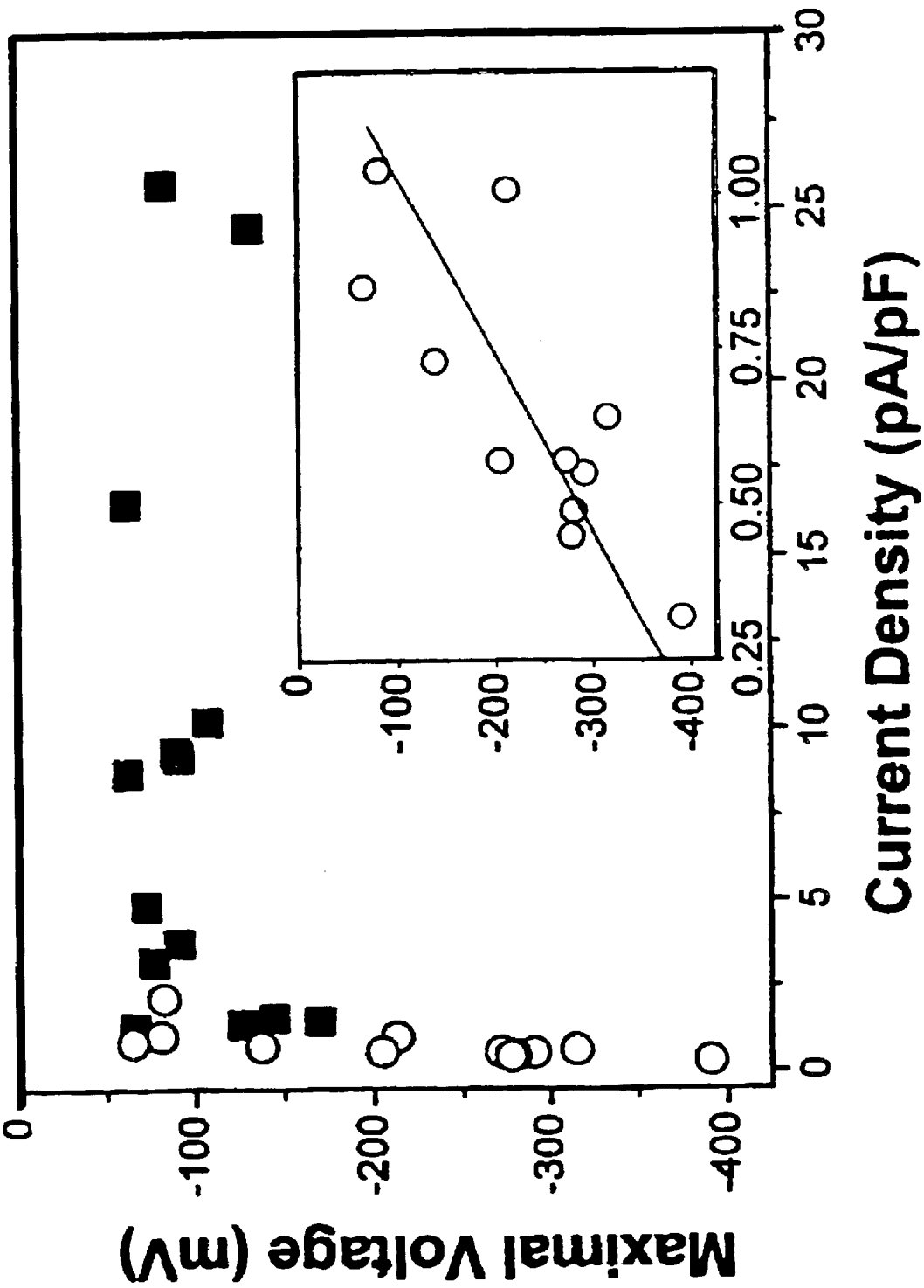

The adult cultures did not beat spontaneously, either under control conditions or after infection with AdHCN2. This was not surprising, given the relatively negative activation relation of the expressed current in the adult cells. However, Ranjan et al. (38) have proposed that native $I_f$ in the adult mammalian ventricle contributes to anode break stimulation. If sufficiently strong, the hyperpolarizing stimulus activates $I_f$. The resultant inward tail current, combined with the voltage dependent block of $I_{K1}$, then causes the membrane potential to overshoot the resting potential in a depolarizing direction upon termination of the stimulus, leading to excitation. Therefore, the susceptibility to anode break excitation of control adult cultures and those infected with AdHCN2 was compared. Using a 20-msec stimulus, the maximal negative potential achieved for a threshold anodal stimulation was measured. Also measured was the $I_f$ density at the end of a 2-sec voltage step up to −125 mV in the same cells. FIG. 9 illustrates that the infected cells more readily exhibited anode break excitation. FIG. 9A illustrates representative control (left, with stimulus time course above) and infected (right) traces of anodal stimuli and resulting action potential upstrokes. The delay between the end of the anodal stimulus and the action potential threshold was not statistically different between control and infected cells (45±10 vs. 58±9 ms, P>0.05). FIG. 9B graphs the relation between maximal negative potential at threshold and $I_f$ or $I_{HCN2}$ density for control (unfilled symbol) and infected (filled symbol) cells. Control cells exhibited an inverse correlation between the maximal negative voltage required for anodal excitation and $I_f$ density (FIG. 9B, inset), supporting the hypothesis that native $I_f$ contributes to anode break excitation. In comparison, in infected cells it was sufficient to hyperpolarize the membrane to approximately −80 mV, i.e. the threshold for expressed HCN2 current. Anode break threshold was independent of expressed current density, indicating that the expressed current was large enough in. all infected cells to generate a sufficient overshoot for achieving excitation at $I_{HCN2}$ threshold. When required stimulus energy was calculated, as the integral of the area from start of the stimulus to threshold of the action potential, there was a significant difference between control and AdHCN2 infected cells (3140±279, n=10, vs. 2149±266 mV·ms, n=12; P<0.05). Neither the required stimulus energy nor the spontaneous rate of cells infected with AdGFP differed from those of control cells (data not shown), indicating that this was not simply an effect of the adenoviral infection. In addition, resting potential did not differ between control, AdHCN2 and AdGFP infected myocytes (data not shown).

Discussion

This study investigated if the distinct activation voltage of $I_f$ in neonatal and adult ventricle was the result of a pronounced difference in the biophysical properties of the HCN2 and HCN4 isoforms when expressed in ventricular myocytes, or whether this developmental difference was due to an influence of the maturational state of the myocyte on an individual isoform, specifically HCN2. The results indicate that while HCN4, which is more prevalent in neonatal than adult ventricle, does activate at less negative voltages than HCN2 when expressed in the neonatal ventricle, this isoform effect is modest. In comparison, when the HCN2 isoform is separately expressed in neonatal and adult ventricular myocytes, the midpoints of activation differ by 18 mV, compared to a difference of 22 mV in the midpoints of activation of the native $I_f$ current in the neonate and adult ventricle in culture. Thus, the developmental difference in pacemaker current voltage dependence under these experimental conditions is largely accounted for by an effect of the myocyte maturational state on the HCN2 isoform, rather than an HCN4/HCN2 isoform switch. Further, this difference in activation voltage results in a marked difference in the physiologic impact of expressed HCN2 current, due to the relative position of the current threshold with respect to the maximum diastolic potential as a function of age.

In investigating this question, first was compared the biophysical characteristics of mouse HCN2 and HCN4 expressed in neonatal rat ventricular myocytes, rather than in a heterologous mammalian expression system such as HEK293 cells. As with prior heterologous expression studies, these data indicate that an inherent difference in the voltage dependence of HCN2 and HCN4, when expressed in myocytes, does not by itself account for the age-dependent difference in voltage dependence. At both ages, HCN2 is the dominant isoform based on RNase protection, although the relative ratio of HCN2/HCN4 message increases developmentally (16). The 9-mV negative shift of HCN2 activation, xrelative to HCN4 (−75 and −66 mV, respectively, using the lipofectin transfection method) in neonatal myocytes is far less than the developmental difference in native current activation. In addition, the kinetics of activation of the native $I_f$ are faster in the neonate than adult, while the activation kinetics of HCN4 are slower than those of HCN2. Thus, a dominant contribution of HCN4 in the neonate, changing to a dominant contribution of HCN2 in the adult, is inadequate to explain the developmental difference in either activation voltage or activation kinetics. It should be noted, however, that this does not preclude an isoform switch as a necessary or contributory component of the developmental change in voltage dependence. It could be that HCN4 would activate at markedly less negative voltages in adult as well as neonatal ventricle, i.e. that only HCN2 is sensitive to the maturational state of the myocyte.

While resolution of this question awaits preparation of an HCN4 adenoviral construct for efficient infection of adult myocytes, it seems unlikely given existing heterologous expression results concerning HCN4, which do not suggest that HCN4 is inherently positive. Admittedly, it is difficult to compare activation voltages between studies, since even with the same preparation considerable differences arise between laboratories as a result of variations in cell preparation and/or recording protocols. Still, it is interesting that HCN4 expression in the neonatal ventricle is much less negative than in any reported mammalian expression study. A midpoint of −66 mV was observed, whereas in other mammalian expression studies reported values ranging from −80 to −109 mV for this isoform (17–20). HCN2 in the neonatal ventricle also activates at less negative voltages than in other mammalian systems, with a midpoint of −78 mV (by tail measurement with adenoviral infection) in the present study, compared to values ranging from −83 to −97 mV (18–20, 39). In those cases where activation voltage of HCN2 and HCN4 were measured in the same study, HCN2 activated either slightly less negatively (18), equivalently (19) or slightly more negatively (20) than HCN4. Thus, while the results largely agree with other studies that reported only a modest difference in activation voltage between HCN2 and HCN4, in general what was observed was less negative activation of both isoforms in the neonatal ventricle, compared to other mammalian expression systems. This suggests that perhaps the neonatal myocyte provides a unique environment, relative to alternative expression systems, allowing for less negative activation. However, at least one oocyte expression study (40) reported HCN2 activation equivalent to that in the neonatal ventricle, with a midpoint of −78 mV, suggesting that other systems also are capable of expressing HCN2 with less negative voltage dependence.

While it is not clear whether it is the neonatal or the adult environment which is unique (or rather they are merely two distinct points on a continuum), it is clear that HCN2 exhibits markedly different voltage dependence when expressed in the two cell preparations, and that this parallels the developmental difference in native $I_f$. Under these experimental conditions, the midpoint of activation of native current in newborn and adult ventricle differed by approximately 22 mV, less than the previously reported difference in threshold value of approximately 40 mV (8). A portion of the difference may result from the 48-hour culture period, since acutely isolated adult myocytes had a midpoint value of activation that was 6 mV more negative. Although this was not a statistically significant difference, it is in keeping with an earlier study that found that extended culture under conditions that caused morphological dedifferentiation of adult myocytes resulted in a marked positive shift of activation voltage (9). In addition, the earlier developmental study specifically used adult epicardial myocytes (8), while the present study used the whole ventricle of the adult heart to obtain a higher yield of viable cells for culture. A gradient of $I_f$ activation, with epicardium more negative than endocardium, has been observed in the canine heart (41). If a similar gradient exists in adult rat ventricle then this also could contribute to the less negative adult values observed in the present study. It remains to be determined if expressed HCN2 current would activate at even more negative voltages if expressed in epicardial myocytes.

The actual midpoints of activation of native $I_f$ in ventricle were −77 and −99 mV in neonate and adult, respectively, compared to values for HCN2 of −78 and −96 mV in these two preparations. Thus, HCN2 activation largely explains the voltage dependence of the native $I_f$. The difference in activation between neonatal and adult ventricle is not secondary to differences in cAMP levels, since saturating cAMP in the pipette shifts the voltage dependence of HCN2 by a comparable amount in the neonate and adult myocytes (17 and 14 mV, respectively). Beyond elimination of basal cAMP as a factor, the basis for the age-dependent difference in HCN2 voltage dependence when expressed in myocytes is unclear. The range of voltage dependence reported for $I_f$ in different cardiac regions or as a function of age or disease is pronounced, and may reflect a combination of mechanisms. Studies of other channels have identified a number of factors that can alter the biophysical properties of native or expressed current, including beta subunits (42, 43), local membrane composition (44), cytoskeletal interactions (45), phosphorylation/dephosphorylation (35, 36, 46) and other post-translational modifications such as truncation (47). The extent to which any of these mechanisms contribute to the variation in voltage dependence of $I_f$ or $I_{HCN2}$ is unknown. In this context, it is interesting that when native $I_f$ is studied in a cell free macro patch activation shifts markedly negative, but treatment of the intracellular face of the patch with pronase shifts activation back in the positive direction by 56 mV (48). In addition, when a large portion of the HCN2 C-terminal that includes the cyclic nucleotide binding domain is deleted, activation shifts positive by 24 mV (49). From these results one can speculate that interactions between cytoplasmic elements of the HCN protein contribute to more negative activation, but that these interactions are minimized in the intact cell, perhaps due to the presence of cytoskeletal elements, a beta subunit or other factors. The extent to which any of these factors actually contribute to the regional or developmental variation in activation voltage remains to be determined. However, if this reasoning is correct, then the factor(s) that contribute to the less negative activation of HCN2 in the neonate do not appear to be substrate limited, since no negative shift in activation voltage (and in fact a slight positive trend) at expression levels that were 2–3 orders of magnitude greater than that typical of native current in this preparation was observed.

The kinetic characteristics of the native current in neonate and adult ventricle also are largely explainable by HCN2, though perhaps not entirely. In the neonate, native current activates with kinetics that are intermediate-between those of HCN2 and HCN4 expressed in these same cells. When the full activation/deactivation relation of expressed HCN2 is compared in neonate and adult, the difference is largely attributable to the difference in voltage dependence of activation. Thus, there does not appear to be an effect of maturational state of the myocyte directly on activation kinetics of expressed current, independent of the effect on voltage dependence of activation. However, native $I_f$ kinetics in adult appear slower than expressed HCN2 kinetics (compare FIGS. 4B and 5B).

Not surprisingly, expressing high levels of HCN2 in a neonatal culture results in a marked increase in spontaneous rate. This is accompanied by a less negative maximum diastolic potential and more pronounced phase 4 slope. The maximum diastolic potential in the HCN2 infected culture corresponds to the threshold voltage of the HCN2 current, indicating that even threshold levels of expressed current are sufficient to balance the contribution of $I_{K1}$ (which is small in neonatal cultures (50)). Expressing HCN2 in adult myocytes does not result in automaticity, either because of the more negative activation range in the adult cells or the greater $I_{K1}$ density at this age. However, it does increase the susceptibility to anode break excitation. In HCN2 infected cultures of adult cells, the maximal negative voltage required during anodal stimulation in order to exhibit anode break excitation corresponds to the threshold voltage of the HCN2 current. Thus, the physiologic impact of overexpression of the HCN gene family in myocardium depends on the threshold voltage of the expressed current.

This threshold voltage, and therefore the physiologic impact of HCN overexpression, to some extent depends on which isoform is expressed (i.e. HCN2 vs HCN4 in neonate). However, effect also is context dependent—with a distinct result, depending on the maturational state of the target tissue. For the same reason, effect is likely to depend on the cardiac region in which the channel is expressed and the disease state of the tissue, since native current is markedly affected by these factors. This has obvious implications for any future efforts to alter cardiac rhythm through the regional overexpression of selective HCN isoforms. It suggests rate can be enhanced by increasing current level, if the expressed current activates at an appropriate threshold voltage in the target tissue. As further insight into the mechanisms regulating the voltage dependence of this gene family is gained, it may be possible to control both the level of current and its activation voltage.

EXPERIMENTAL DETAILS EXAMPLE 2

MiRP1: A Beta Subunit for the HCN Ion Channel Subunit Family Enhances Expression and Speeds Kinetics The HCN (Hyperpolarization-activated Cyclic Nucleotide gated) family of ion channel subunits has been identified as the molecular correlate of the currents $I_f$ in heart and $I_h$ and $I_q$ in neurons (14,15,26). However, a number of ion channels are heteromultimers of a large a subunit (like the HCN family members) and smaller β subunits. The cardiac delayed rectifiers $I_{kr}$ (51) and $I_{ks}$ (52) are examples of this basic principle. Their α subunits derive from the ERG and KCNQ families respectively, but both also contain β subunits from a family of single transmembrane spanning proteins called minK and MiRPs (minK related peptides).

MiRP1 enhances expression and speeds the kinetics of activation of the HCN family of channel subunits. RNase protection assays (RPAs) show that MiRP1 mRNA is prevalent in the primary cardiac pacemaking region, the sinoatrial node, and barely detectable in ventricle. Coimmunoprecipitation indicates that MiRP1 forms a complex with HCN1. Taken together, these results suggest that MiRP1 is a β subunit for the HCN family of ion channel protein subunits, and that it is likely to be an important regulator of cardiac pacemaker activity.

A. Heterologous Expression in Xenopus Oocytes cRNA encoding mouse HCN1 or HCN2, rat MiRP1 with or without an HA tag at the carboxy-terminal and rat minK were transcribed by using the mMessage mMachine kit (Ambion, Austin, Tex.). *Xenopus laevis* oocytes were isolated, injected with 2–5 ng (50–100 nl) of cRNA, and maintained in Barth medium at 18° C. for 1–2 days. For experiments using both HCN1 or HCN2 and MiRP1 or minK, the respective cRNAs were injected in 1:0.04–1 ratio. Electrophysiologic studies on oocytes employed the two-microelectrode voltage clamp. The extracellular recording solution (OR2) contained: 80 mM NaCl, 2 mM KCl, 1 mM $MgCl_2$, and 5 mM Na-HEPES (pH 7.6). Group data are presented as means ±SEM. Tests of statistical significance for midpoint and slope of activation curves were performed using unpaired Student's t-tests. P<0.05 is considered significant.

B. Rnase Protection Assays

The procedures for the preparation of total RNA from rabbit heart tissues and the performance of the RNase protection assays was similar to those described previously (53). Brain total RNA was obtained commercially from Clontech, and total RNA was isolated from left ventricle, right atrium and brain using SV Total RNA System (Promega).

For each experiment 2 μg of total RNA was used. A cyclophilin probe was used in each experiment as an internal control over sample loss. RNA expression was quantified directly from dried RNase protection assay gels using a Storm phosphorimager (Molecular Dynamics), normalized to the cyclophilin signal in each lane. The MiRP1 signal consisted of two protected fragments in each rabbit tissue where MiRP1 was detected. The presence of two bands is likely the result of the degenerate PCR primers, based on mouse and human sequences, used for the cloning of the RPA probes. The combined intensity of both bands was used in the quantification.

C. Protein Chemistry

Membrane protein preparation. All steps were performed in ice. 25 oocytes were washed with Ringer solution (96 mM NaCl, 1.8 mM $CaCl_2$, 5 mM Hepes (pH 7.4) and lysed by vortexing with 1 ml lysis buffer 1 (7.5 mM $Na_2HPO_4$ (pH 7.4), 1 mM EDTA) with protease inhibitors (aprotinin, leupeptine and pepstatin A, 5 μg/ml of each, and 1 mM PMSF). The lysate was centrifuged for 5 min at 150× g to remove yolk proteins and subsequently for 30 min at 14000× g. The membrane pellet was washed with lysis buffer 1 and resuspended in 1 ml of lysis buffer 2 (50 mM Tris-HCl (pH 7.5), 150 mM NaCl, 5 mM EDTA, 50 mM NaF, 50 mM Na pyrophosphate, 100 mM $KH_2PO_4$, 10 mM Na molybdate, 2 mM Na orthovanadate, 1% triton X-100, 0.5% NP40) with the same set of protease inhibitors as lysis buffer 1. Protein concentration of the membrane fractions was determined by the Lowry method.

Immunochemistry. For western blot analysis, proteins associated with oocyte membrane fractions were separated on 10% SDS/PAGE (for HCN1) or on 16.5% tricine-SDS/PAGE (for MiRP1 (54)), and electroblotted to Hybond ECL™ nitrocellulose membranes (Amersham Pharmacia Biotech). Blocking and antibody incubations were done in PBST. The rabbit HCN1 antibodies (Quality Controlled Biochemicals) and the rat anti-HA high affinity antibodies (Roche Molecular Biochemicals) were used at 1:5000 and at 1:500 dilution, respectively. Secondary anti-rabbit (Kirkegaard Perry Laboratories, Maryland, USA) and anti-rat Ig-POD, Fab fragments (Boehringer Mannheim Biochemica) coupled to horseradish peroxidase were used at 1:10000 or 1:2000 dilution, respectively. The immunoreactive protein bands were visualized using Lumi-Light$^{PLUS}$ Western Blotting Substrate (Roche Molecular Biochemicals). The immunoprecipitation reactions were performed using 250 μg of membrane protein fractions and 10 μl of HCN1 antibodies cross-linked to protein A/G PLUS-Agarose (Santa Cruz Biotechnology, Inc.) with dimethylpimelimidate.

Results

Figure 10A:
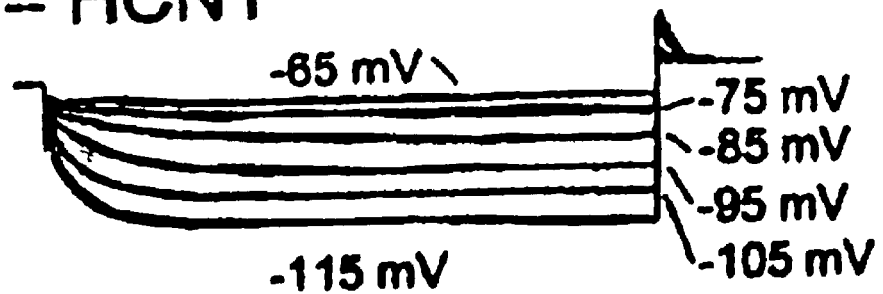
FIGS. 10A–H: functional expression of HCN1 and HCN2 channels with and without minK and MiRP1 in Xenopus oocytes. The holding potential is −35 mV, and the voltage increment is always 10 mV. A: 5 ng HCN1 cRNA injection and test pulses 3-seconds long from −65 mV to a maximum voltage of −115 mV. B: 5 ng HCN1 plus 0.2 ng minK injection with test pulses 3-seconds long from a minimum voltage of −55 mV to a maximum voltage of −115 mV. C: 5 ng HCN1 plus 0.2 ng MiRP1 injection with test pulses 3-seconds long from −55 mV to −115 mV. D: 5 ng HCN2 cRNA injection with test pulses 8-seconds long from −55 mV to −95 mV. E: 5 ng HCN2 plus 0.2 ng minK injection with test pulses 8-seconds long from −65 mV to −105 mV. F: 5 ng HCN2 plus 0.2 ng MiRP1 injection with test pulses 8-seconds long from −55 mV to −95 mV. G: the maximum conductance of the tail current obtained by dividing its amplitude by the driving force at that potential.
Figure 10B:
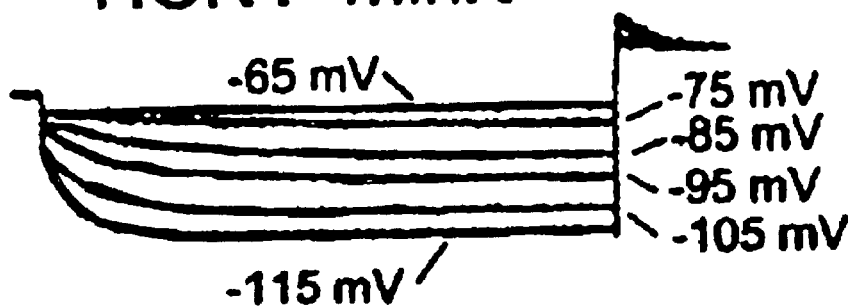
Figure 10C:
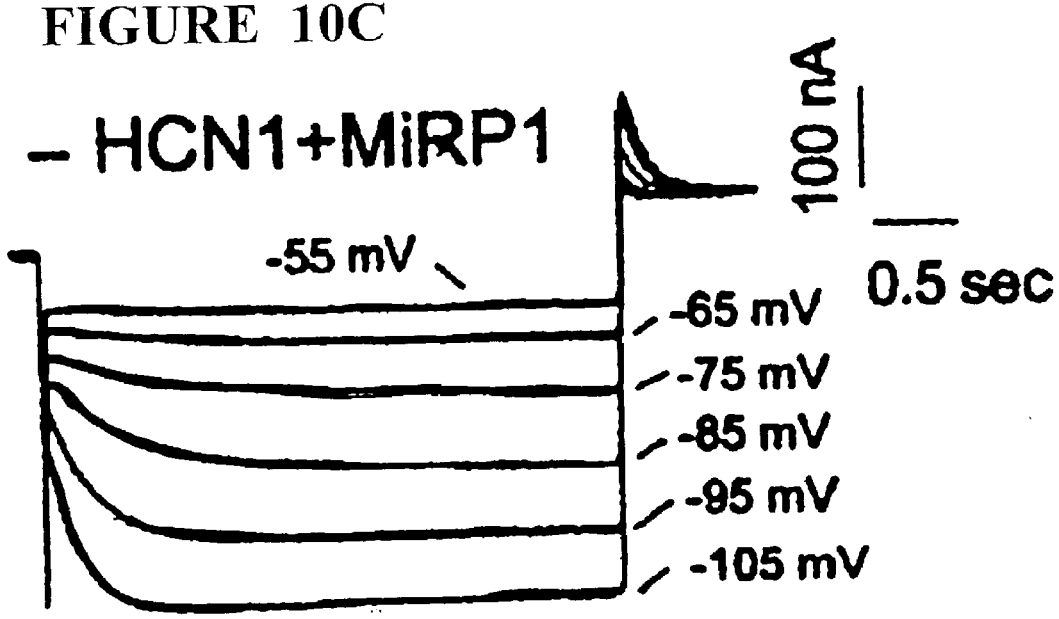
Figure 10D:
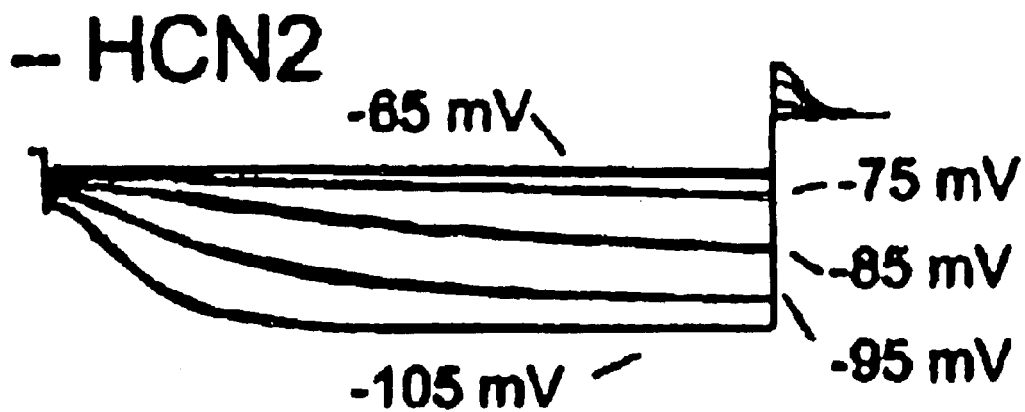
Figure 10E:
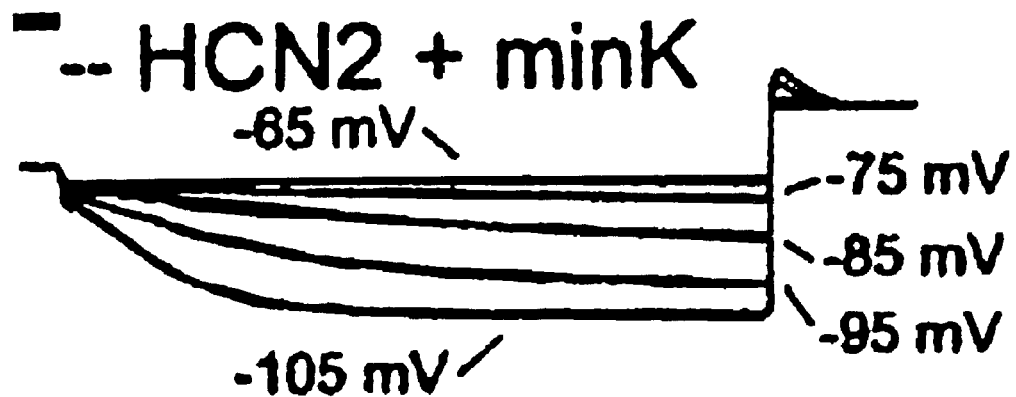
Figure 10F:
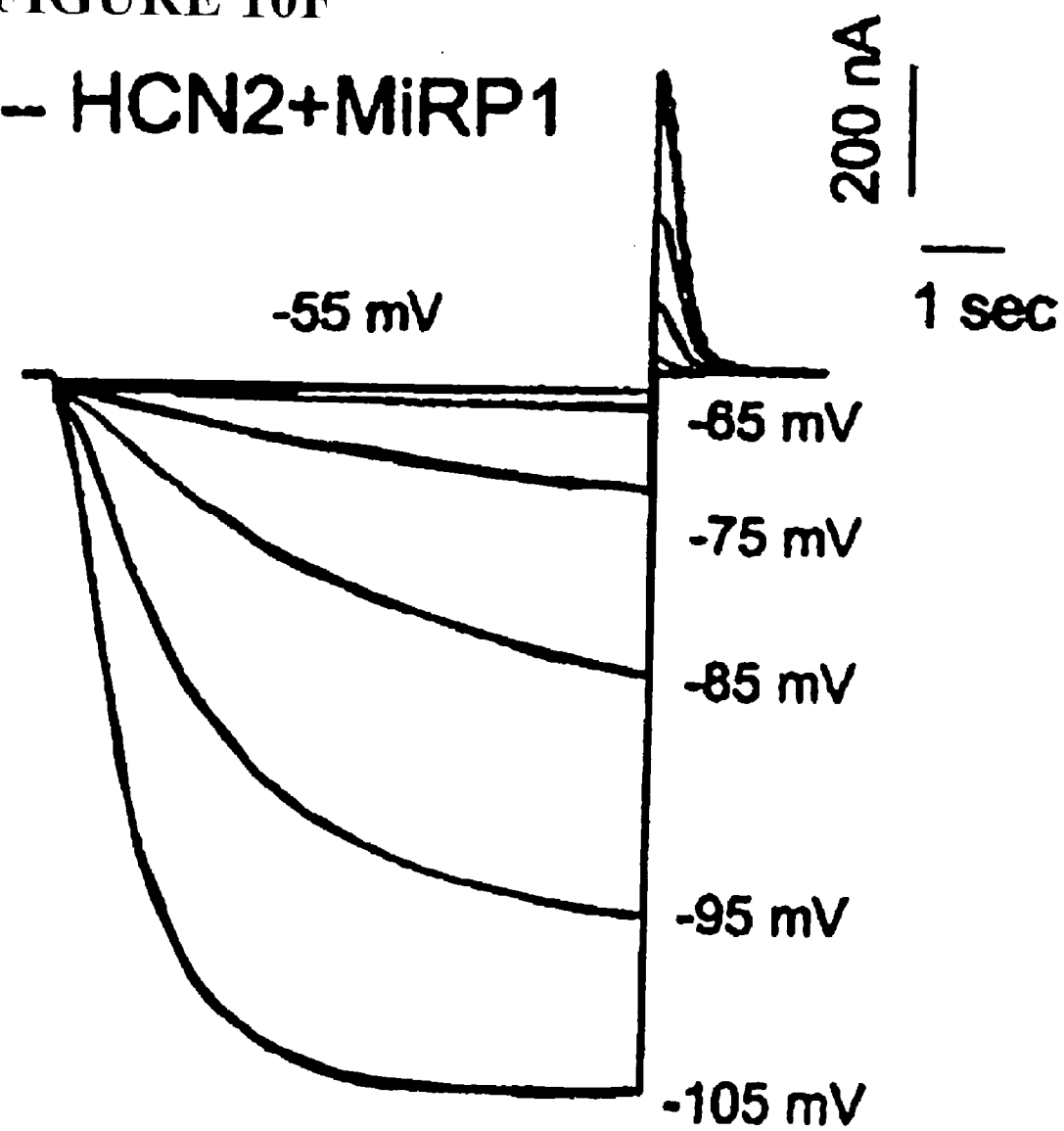
Figure 10H:
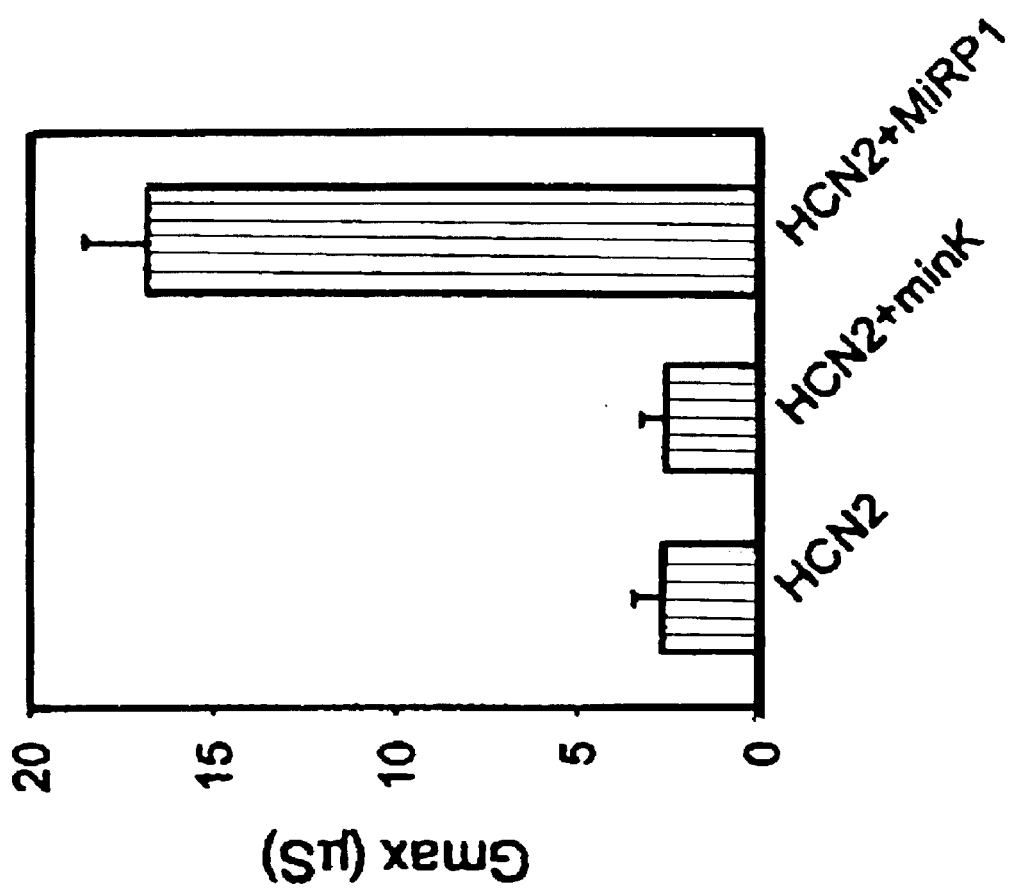
Figure 10G:
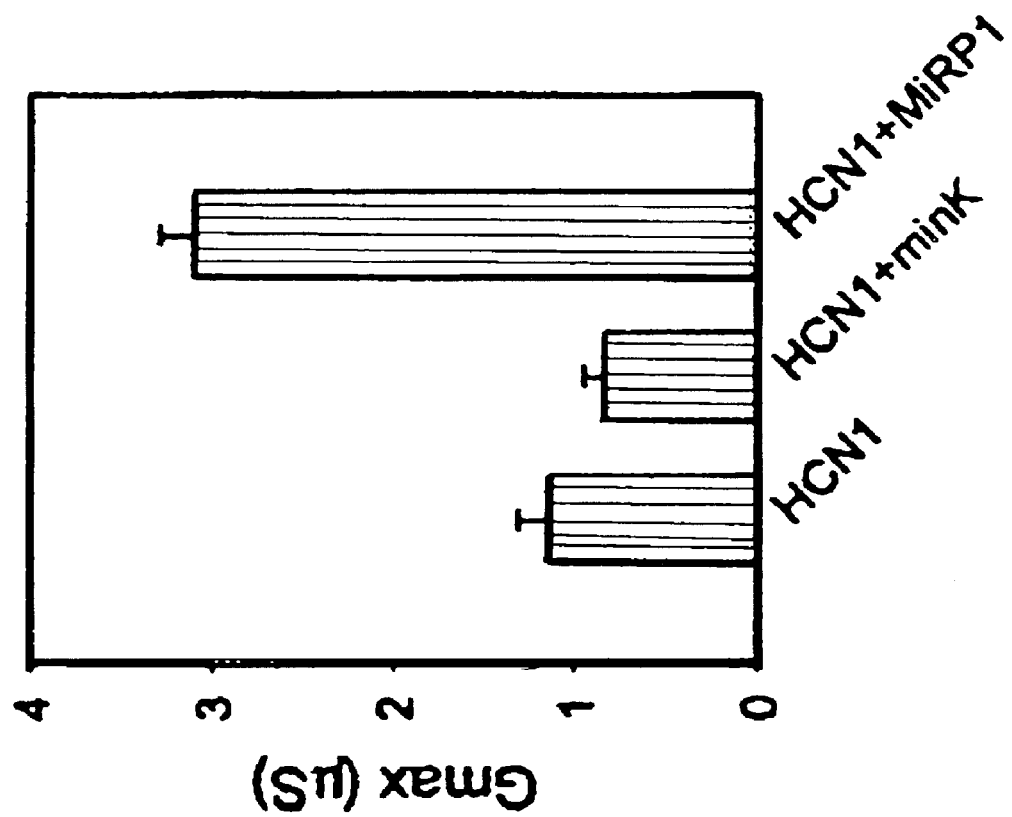

Xenopus oocytes were employed as a heterologous expression system and the expression of HCN1 and HCN2 individually and coexpressed with either minK (the minimal K channel protein, the first identified member of the single transmembrane spanning proteins family) or with MiRP1 was examined. The results are shown in FIG. 10. Both HCN1 (FIG. 10A) and HCN2 (FIG. 10D) express a small current when injected alone. Coexpression of either HCN1 (FIG. 10B) or HCN2 (FIG. 10E) with minK results in similar, low levels of current expression. However, a much larger current is observed when either HCN1 (FIG. 10C) or HCN2 (FIG. 10F) is coexpressed with MiRP1. Injection of MiRP1 by itself did not induce a current nor did injection with 100 nl of $H_2O$ (not shown). The complete set of results for the expression studies of HCN1 and HCN2 with or without minK and MiRP1 are illustrated in FIG. 10G and FIG. 10H. The maximal conductance is calculated by dividing the current onset at the most negative potential by the driving force (the reversal potential was measured in each oocyte). The results demonstrate an almost threefold enhancement of HCN1 conductance when HCN1 is coexpressed with MiRP1, whereas MiRP1 enhances expression of HCN2 by more than fivefold. Coexpression of either HCN1 or HCN2 with minK does not enhance HCN1 or HCN2 expression. Thus the enhancement of expression is specific for MiRP1.

Figure 11B:
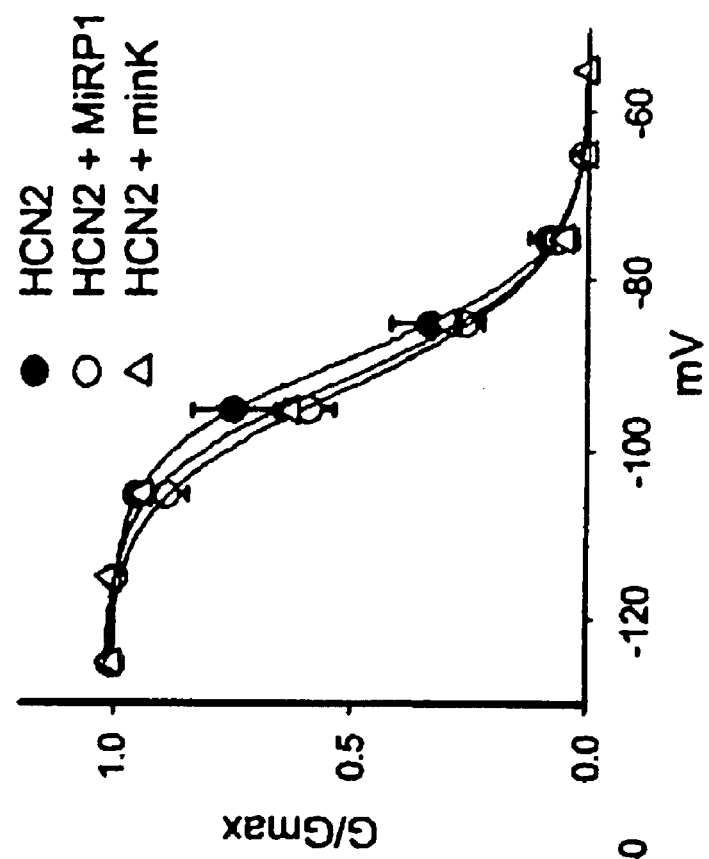
FIGS. 11A–F: gating properties of the expressed channels. A: activation curves of HCN1 alone and HCN1 coexpressed with MiRP1. The inset shows the representative tail currents used to construct the activation curve. B: activation curves of HCN2 alone and HCN2 coexpressed with MiRP1. C: sample data illustrating activation kinetics of HCN1 alone and HCN1 coexpressed with MiRP1. D: sample data illustrating activation kinetics of HCN2 alone and HCN2 coexpressed with MiRP1. E: plot of activation and deactivation (in box) time constants for HCN1 alone and HCN1+ MiRP1. F: same as (E) but for HCN2 and HCN2+MiRP1.
Figure 11A:
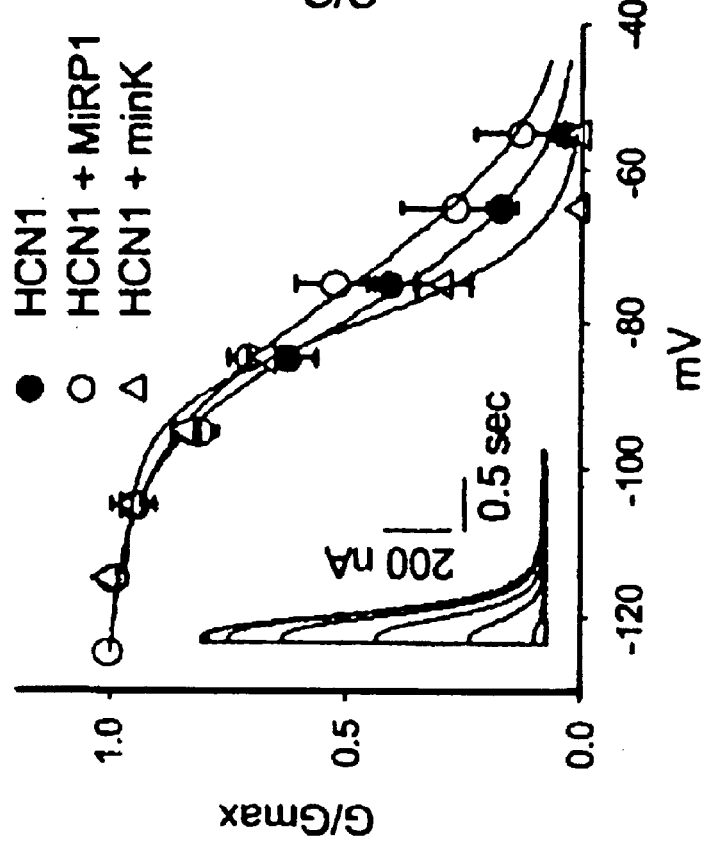
Figure 11D:
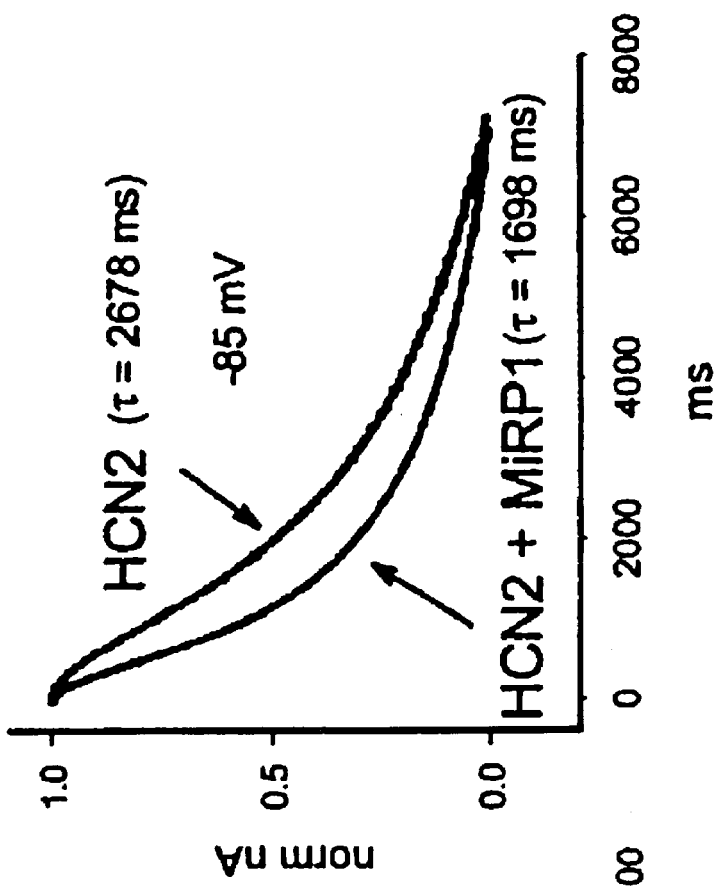
Figure 11C:
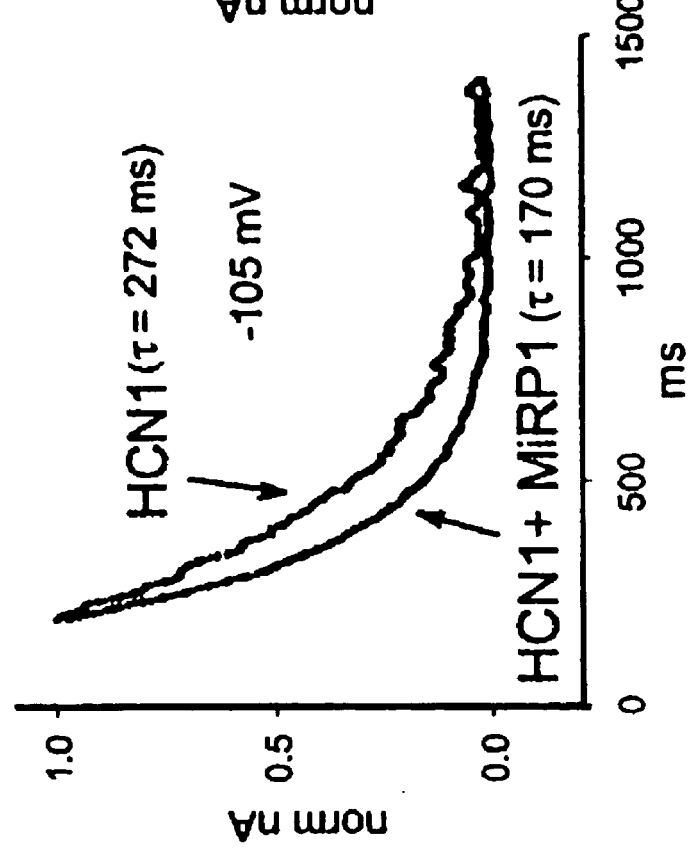
Figures 11E, 11F:
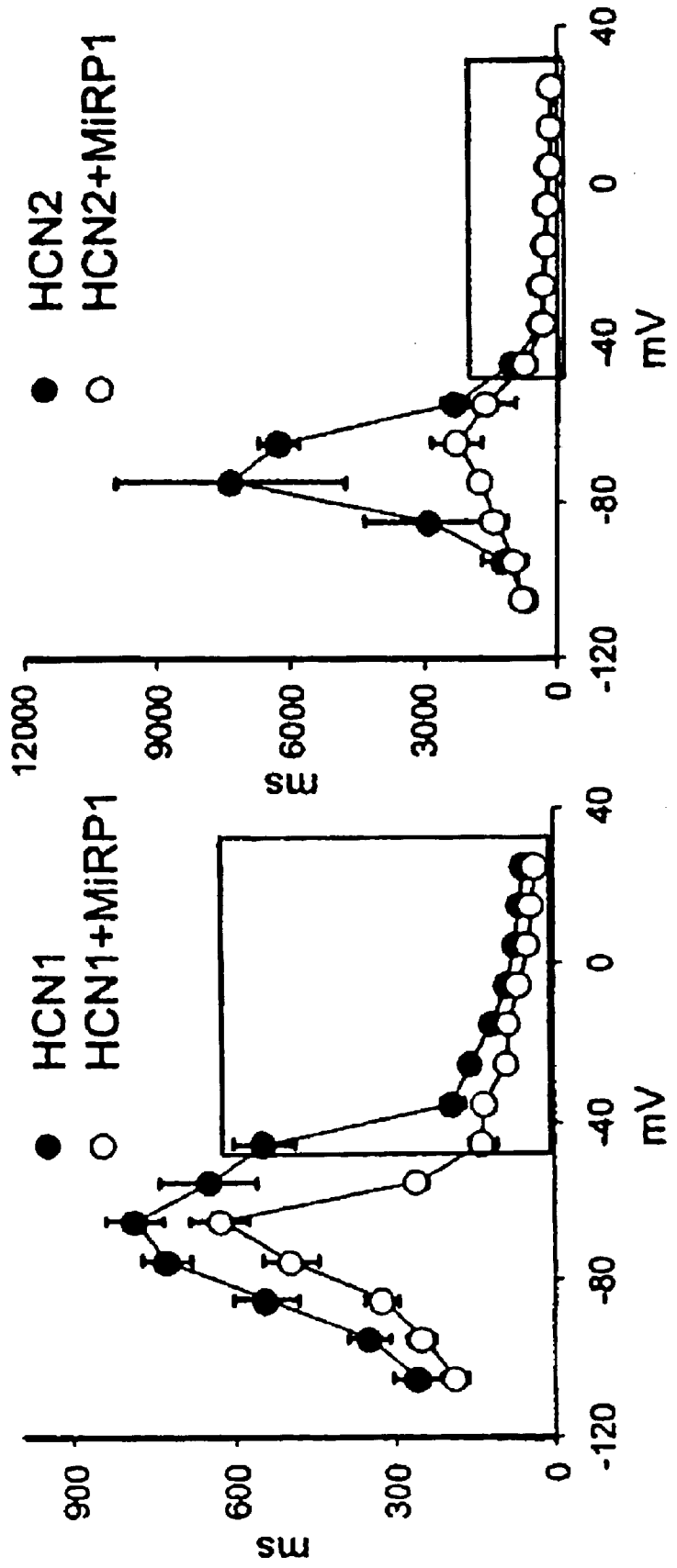

Next was examined the gating properties of MiRP1 coexpressed with either HCN1 or HCN2. The results are presented in FIG. 11. Isochronal activation curves were constructed from tail currents recorded at −10 mV in response to 3 (for HCN1) or 8 (for HCN2) second long hyperpolarizing test pulses. The results demonstrate no significant difference in midpoint but statistically indicate a shallower slope for the activation of HCN channels coexpressed with MiRP1 (FIGS. 11A and 11B, see figure legends for details).

Also, the kinetics of activation and deactivation was examined(see FIG. 11C–FIG. 11F). Raw data are shown for activation of both HCN1 (FIG. 11C) and HCN2 (FIG. 11D), MiRP1 decreases the time constant of activation. The average of all the results on activation and deactivation (indicated by the encircled box) are provided in FIGS. 11E and 11F. Coexpression with MiRP1 accelerates both processes.

The rectification properties of HCN1 or HCN2 expressed with or without MiRP1 were also studied. Coexpression of either HCN1 or HCN2 with MiRP1 did not alter the linearity of the fully activated current-voltage relationship (not shown).

Figure 12A:
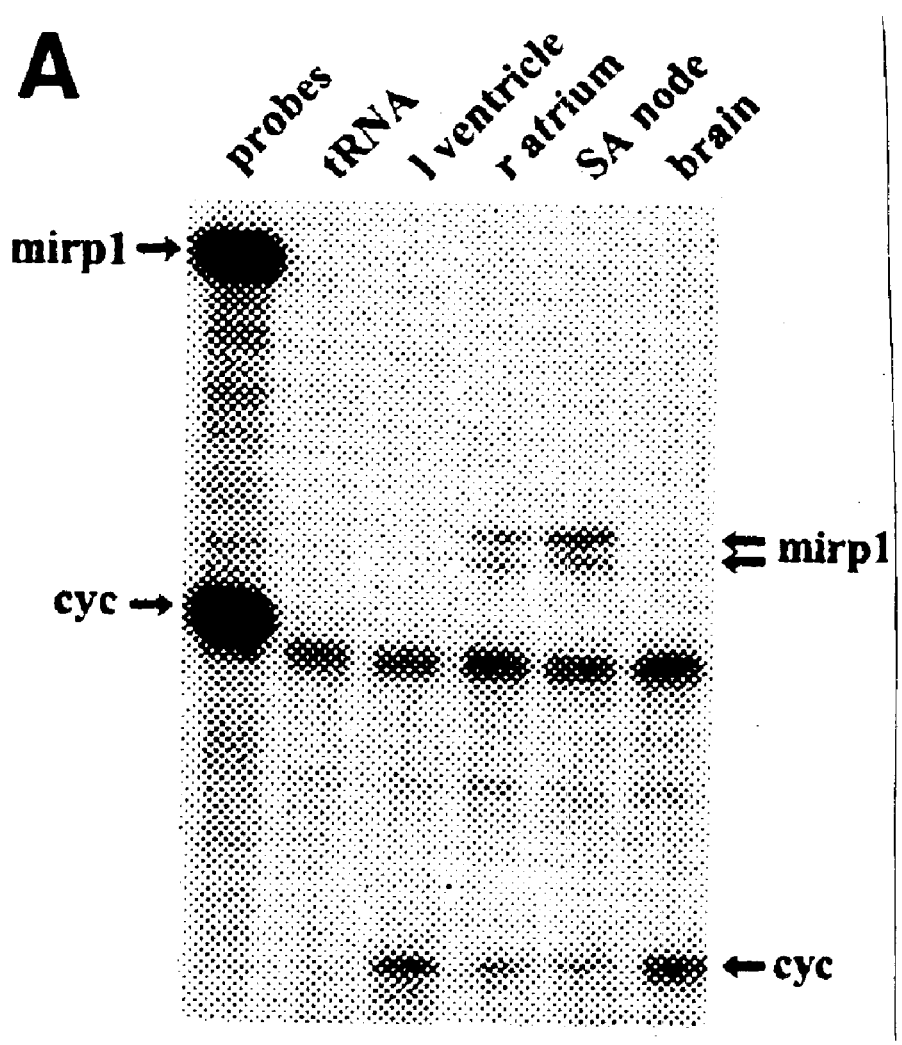
FIGS. 12A–B: MiRP1 mRNA expression in rabbit as determined by RNase protection assays. A: represents an example of a representative RPA performed on 2 µg of total RNA isolated from left ventricle, right atrium, SA node and whole brain. B: histogram showing the relative abundance of MiRP1. Data are normalized to the cyclophilin protected fragment; values are the means of three independent mRNA samples and the error bars are SEM.
Figure 12B:
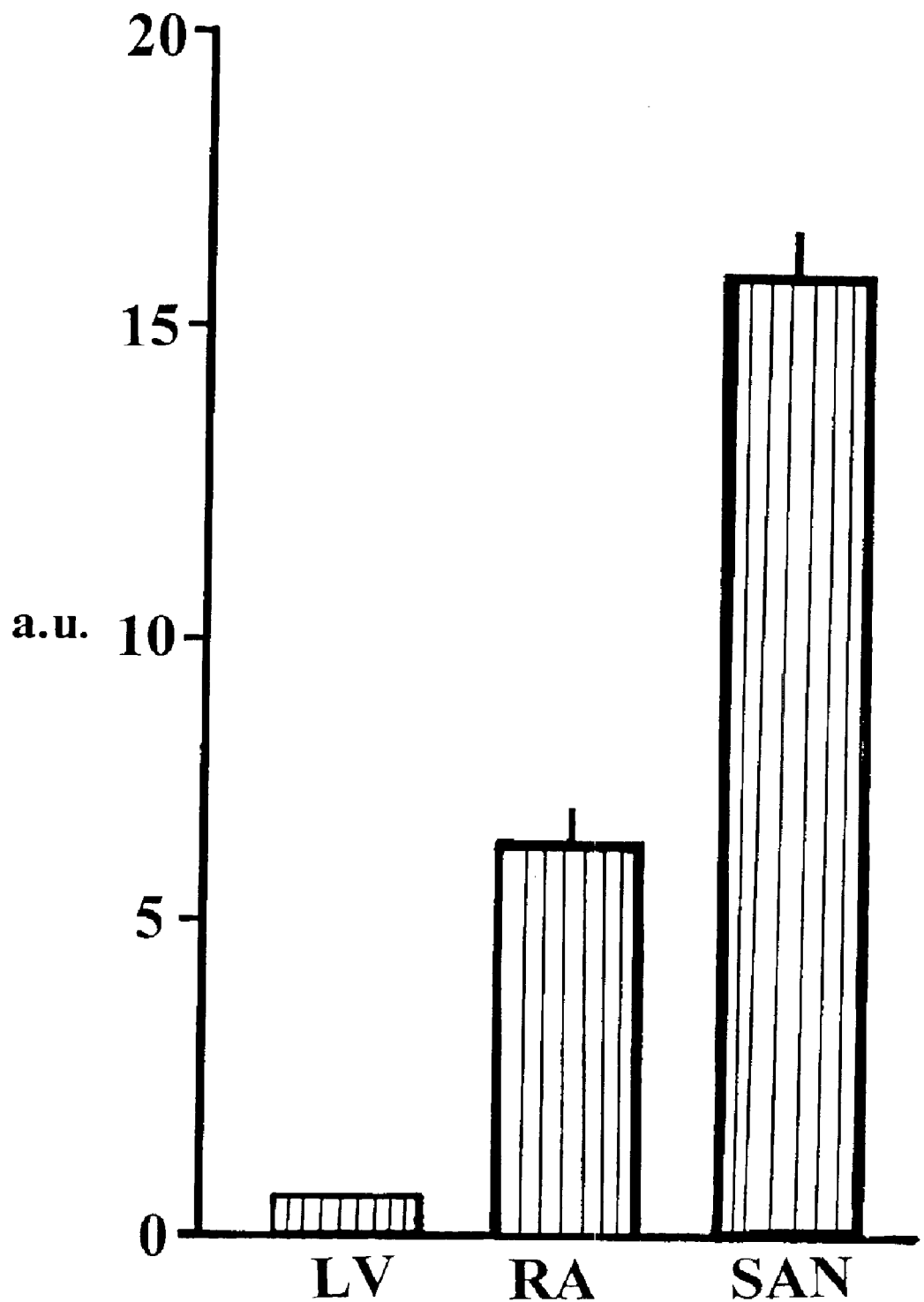

Previous studies examining the potential role of MiRP1 in generating $I_{kr}$ employed Northern Blot analysis to demonstrate the presence of MiRP1 mRNA in whole rat heart (51). If MiRP1 also regulates $i_f$ current expression in vivo, mRNA for MiRP1 should be prominent in regions where if currents are large. RNase protection assays was employed to quantify the distribution of MiRP1 transcripts in SA node, right atrium and ventricle of the rabbit heart. The results are provided in FIG. 12. MiRP1 transcript levels are highest in the SA node, atrial levels are about 40% of those in SA node, while ventricular levels are barely detectable (<4% of SA node).

Here, it was demonstrated that a complex probably exists between members of the HCN family and MiRP1, which shows that MiRP1 could be a β subunit for the HCN family. This question was chosen to be pursued with HCN1 as there are antibodies (see Methods) against this family member.

Figure 13A:
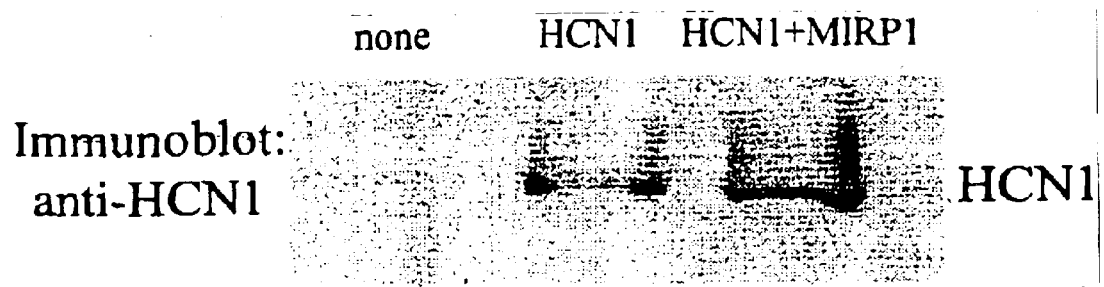
FIGS. 13A–C: western blots showing protein expression of HCN1 channel subunits with and without MiRP1 in Xenopus oocytes following immunoprecipitation with the HCN1 ion channel subunit. A: proteins in oocyte membranes fractionated and probed with anti-HCN1 antibody. B: oocyte membrane protein probed with anti-HA antibody. C: products of IP reactions by anti-HCN1 antibody from membrane protein from oocytes injected with HCN1, MiRP1 or by both cRNAs probed with anti-HA antibody.
Figure 13B:
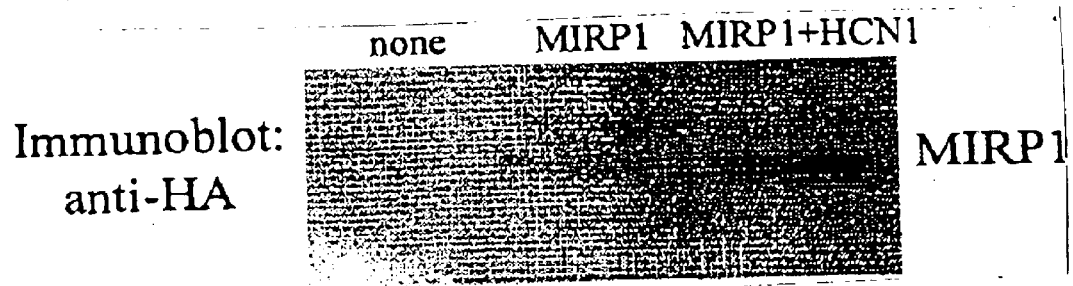

The HCN1 antibody recognizes a single polypeptide with an apparent molecular mass of 145 kDa (possibly glycosylated (55)). MiRP1, HA epitope-tagged at the carboxy-terminal end, was recognized by anti-HA high affinity antibodies as a 13.5 kDa band. Both proteins were localized in the membrane fraction, and protein expression was enhanced (about 2-fold) when they were co-expressed together (FIGS. 13A and 13B).

Figure 13C:
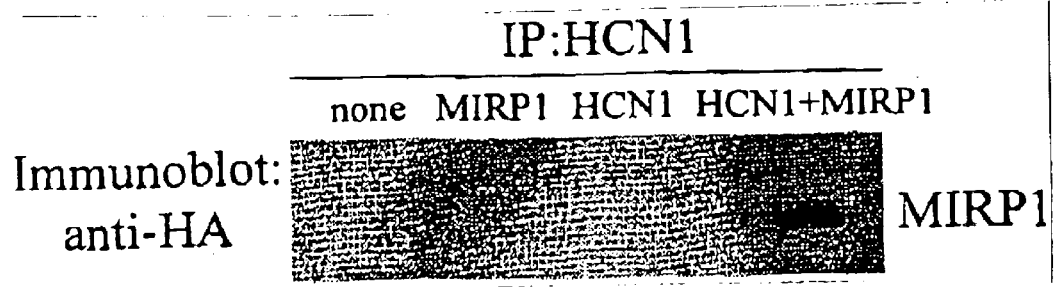

To test whether a complex of HCN1 and MiRP1 might exist in a heterologous expression system, coimmunoprecipitation experiments were performed using membrane fractions of oocytes injected with HCN1 alone, MiRP1 alone, or with both cRNAs, FIG. 13C shows the immunoprecipitation products tested by western blot analysis. The presence of MiRP1 in the anti-HCN1 immunoprecipitate only for oocytes injected by both HCN1 and MiRP1 cRNAs, together with its absence in oocytes injected by one of these mRNAs, indicates that MiRP1 was pulled down by anti-HCN1 antibody most likely because it was complexed with HCN1.

The results demonstrate that the proteins are colocalized as a complex in the membrane and enhance each other's expression. This strongly suggests that MiRP1 is a β subunit for the HCN family of ion channel subunits.

Discussion

MiRP1 is a member of a family of single transmembrane spanning proteins that have been demonstrated to alter expression and serve as a β subunit of both KCNQ (minK) and ERG (MiRP1) family members (51,53). In these previous studies, as in this study, the minK family member altered gating and was demonstrated to be a beta subunit by coimmunoprecipitation.

Here, it has been shown that minK does not affect the properties of HCN1 and HCN2 channels expressed in Xenopus oocytes. MiRP1, on the other hand, dramatically enhances the current expression of both HCN subunits and hastens the kinetics of current activation and deactivation. A speeding of deactivation kinetics is also seen when MiRP1 associates with HERG to form $I_{kr}$ (51). The data presented here also show, that MiRP1 and HCN1 probably form a complex in the membrane.

Pacemaker activity in the rabbit sinus node is generated by a net inward current of only a few pA (56). This net inward current is due to the balance of inward and outward currents more than an order of magnitude larger. Although the biophysical properties of each of the component currents is known, how this fine balance is achieved remains unknown. The results presented here show that a single beta subunit may control the expression of two important pacemaker currents, the outward $I_{kr}$, and the inward $I_f$. If this is the case, it is possible that MiRP1 serves as an important regulator of cardiac pacemaker rate.

Although one preferred embodiment of the invention is described, the invention is not so limited, as variations and modifications will occur to those skilled in the art.

The scope of the invention is determined by way of the appended claims.

REFERENCES

1. DiFrancesco D: The cardiac hyperpolarizing-activated current, $I_f$: Origins and developments. *Prog. BiophysMol. Biol.* Vol. 46, No. 3, 1985, pages 163–183.
2. Zhou Z and Lipsius S L: Effect of isoprenaline on $I_f$ current in latent pacemaker cells isolated from cat right atrium: ruptured vs. perforated patch whole-cell recording methods. *Pflugers Arch.* Vol. 423, No.5 Pt. 6, June 1993, pages 442–447.
3. Thuringer D, et al.: A hyperpolarization-activated inward current in human myocardial cells. *JmolCell. Cardiol.* Vol. 24, No. 5, May 1992, pages 451–455.
4. Porciatti F, et al.: Block of the pacemaker current $I_f$ in single human atrial myocytes and the effect of beta-adrenoceptor and A1-adenosine receptor stimulation. *Br Jpharmacol.* Vol. 122, No. 6, February 1991, pages 963–969.
5. Yu H, et al.: Pacemaker current exists in ventricular myocytes. *Circ. Res.* Vol. 72, No. 1, January 1993, pages 232–236.
6. Cerbai E, et al.: The properties of the pacemaker current $I_f$ in Human Ventricular Myocytes are modulaed by Cardiac Disease. *Jmol. Cell Cardiol.* Vol. 33, No. 3, March 2001, pages 441–448.
7. DiFrancesco D: Generation and control of cardiac pacing: the pacemaker current. *Tends Cardiovasc. Med.* Vol. 1, 1991, pages 250–255.
8. Robinson R B, et al.: Developmental change in the voltage dependence of the pacemaker current, $I_f$, in rat ventricle cells. *Pflugers Arch.* Vol. 433, 1991, pages 533–535.
9. Fares N, et al.: Characterization of a hyperpolarization-activated current in dedifferentiated adult rat ventricular cells in primary culture. *J. Physiol.* Vol. 506, No. 1, Jan. 1, 1998, pages 73–82.
10. Cerbai E, et al.: Influence of postnatal-development on $I_f$ occurrence and properties in neonatal rat ventricular myocytes. *Cardiovasc. Res.* Vol. 42, No. 2, May 1999, pages 416–423.
11. Cerbai E, et al.: Characterization of the hyperpolarization-activated current, $I_f$, in ventricular myocytes isolated from hypertensive rats. *J. Physiol.* Vol. 481, No. 3, Dec. 15, 1994, pages 585–591.
12. Cerbai E, et al.: Characterization of the hyperpolarization-activated current, $I_f$, in ventricular myocytes from human failing heart. *Circulation.* Vol. 95, No. 3, Feb. 4, 1997, pages 568–571.
13. Santoro B, et al.: Interactive cloning with the SH3 domain of N-src identifies a new brain specific ion channel protein, with homology to Eag and cyclic nucleaotide-gated channels. *Proc. Natl. Sci. USA.* Vol. 94, No. 26, Dec. 23, 1997, pages 14815–14820.
14. Ludwig A, et al.: A family of hyperpolarization-activated mammalian cation channels. *Nature.* Vol. 393, No. 6685, Jun. 11, 1998, pages 587–591.
15. Santoro B, et al.: Identification of a gene encoding a hyperpolarization-activated pacemaker channel of brain. *Cell.* Vol. 93, No. 5, May 29, 1998, pages 717–729.
16. Shi W, et al.: Distribution and Prevalence of hyperpolarization-activated cation channel (HCN) mRNA Expression in Cardiac Tissues. *Circ. Res.* Vol. 85, No. 1, Jul. 9, 1999, pages e1–e6.
17. Ishii T M, et al.: Molecular characterization of the hyperpolarization-activated cation channel in rabbit heart sinoatrial node. *J. Biol. Chem.* Vol. 264, No. 18, Apr. 30, 1999, pages 12835–12839.
18. Ludwig A, et al.: Two pacemaker channels from human heart with profoundly different activation kinetics. *EMBO J.* Vol. 18, No. 9, May 4, 1999, pages 2323–2329.
19. Moosmang S, et al.: Cellular expression and functional characterization of four hyperpolarization-activated pacemaker channels in cardiac and neuronal tissues. *Eur. J. Biochem.* Vol. 268, No. 6, March 2001, pages 1646–1652.
20. Altomare C, et al.: Allosteric voltage-dependent gating of HCN channels. *Biophys. J.* Vol. 80, 2001, pages 241a.
21. Protas L, et al.: Chronic neuropeptide Y exposure increases L-type Ca current in neonatal rat cardiomyocytes. *Am. J. Physiol.* Vol. 277, No. 3 Pt. 2, September 1999, pages H940–H946.
22. Kuznetsov V, et al.: β 2-adrenergic receptor actions in neonatal and adult rat ventricular myocytes. *Circ. Res.* Vol. 76, No. 1, January 1995, pages 40–52.
23. Ellingston O, et al.: Adult rat ventricular myocytes cultured in defined medium: phenotype and electromechanical function. *Am. J. Physiol.* Vol. 265, No. 2 Pt. 2, August 1993, pages H747–H754.
24. Ng P, et al.: An enhanced system for construction of adenoviral vectors by the two-plasmid rescue method. *Hwn.Gene Ther.* Vol. 11, No. 5, Mar. 20, 2000, pages 693–699.
25. He T C, et al.: A simplified system for generating recombinant adenoviruses. *Proc. Natl. Acad. Sci. USA.* Vol. 95, No. 5, Mar. 3, 1998, pages 2509–2514.
26. Santoro B, et al.: The HCN gene family: molecular basis of the hyperpolarization-activated pacemaker channels. *Ann. NY Acad. Sci.* Vol.868, Apr. 30, 1999, pages 741–764.
27. Accili E A, et al.: Properties and modulation of $I_f$ in newborn versus adult cardiac SA node. *Am. J. Physiol.* Vol. 272, 1991, pages H1549–H1552.
28. Qu J, et al.: Sympathetic innervation alters activation of pacemaker current ($I_f$) in rat ventricles. *J. Physiol.* Vol. 526, No. 3, Aug. 1, 2000, pages 561–569.
29. Cui J, et al.: Gating of IsK expressed in Xenopus oocytes depends on the amount of mRNA injected. *Gen. Physiol.* Vol. 104, No. 1, July 1994, pages 87–105.
30. Guillemare E, et al.: Effects of the level of mRNA expression on biophysical properties, sensitivity to 30. neurotoxins, and regulation of the brain delayed-rectifier K+ channels Kv1.2. *Biochemistry*. Vol. 31, No. 49, Dec. 15, 1992, pages 12463–12468.

31. Honore E, et al.: Different types of K+ channel current are generated by different levels of a single mRNA. *EMBO J.* Vol. 11, No. 7, July 1992, pages 2465–2471.

32. Moran O, et al.: Level of expression controls modes of gating of a K+ channel. *FEBS Lett.* Vol. 302, No. 1, May 4, 1992, pages 21–25.

33. DiFrancesco D, et al.: Direct activation of cardiac pacemaker channels by intracellular cyclic AMP. *Nature*. Vol. 351, No. 6322, May 9, 1991, pages 145–147.

34. Kaupp U B, et al.: Molecular diversity of pacemaker ion channels. *Annu, Rev. Physiol.* Vol. 63, 2001, pages 235–257.

35. Chang F, et al.: Effects of protein kinase inhibitors on canine Purkinje fibre pacemaker depolarization and the pacemaker current $I_f$. *J. Physiol.* Vol. 440, 1991, pages 367–384.

36. Yu H, et al.: Phosphatase inhibition by calyculin A increases $I_f$ in canine Purkinje fibers and myocytes. *Pflugers Arch.* Vol. 422, No. 6, March 1993, pages 614–616.

37. Accili E A, et al.: Differential control of the hyperpolarization-activated current ($I_f$) by intracellular cAMP and phosphatase inhibition. *J. Physiol.* Vol. 491, 1996, pages 115.

38. Ranjan R, et al.: Mechanism of anode break stimulation in the heart. *Biophys. J.* Vol. 74, No. 4, April 1998, pages 1850–1863.

39. Moroni A, et al.: Kinetic and ionic properties of the human HCN2 pacemaker channel. *Pflugers Arch.* Vol. 439, No. 5, March 2000, pages 618–626.

40. Santoro B, et al.: Molecular and functional heterogeneity of hyperpolarization-activated pacemaker channels in the mouse CNS. *J neurosci.* Vol. 20, No. 14, Jul. 15, 2000, pages 5264–5275.

41. Shi W, et al.: The distribution and prevalence of HCN isoforms in the canine heart and their relation to the voltage dependence of $I_f$ *Biophys. J.* Vol. 78, 2000, pages 353A.

42. Melman Y F, et al.: Structural determinants of KvLQT1 control by the KCNE family of proteins. *J Biol Chem.* Vol. 276, No. 9, Mar. 2, 2001, pages 6439–6444.

43. Tinel N, et al.: KCNE2 confers background current characteristics to the cardiac KCNQ1 potassium channel. *EMBO J.* Vol. 19, No. 23, Dec. 1, 2000, pages 6326–6330.

44. Martens J R, et al.: Differential targeting of Shaker-like potassium channels to lipid rafts. *Biol Chem.* Vol. 275, No. 11, Mar. 17, 2000, pages 7443–7446.

45. Chauhan V S, et al.: Abnormal cardiac Na(+) channel properties and QT heart rate adaptation in neonatal ankyrin(B) knockout mice. *Circ. Res.* Vol. 86, No. 4, Mar. 3, 2000, pages 441–447.

46. Walsh K B, et al.: Disctinct voltage-dependent regulation of heart-delayed $I_K$ by protein kinases A and C. *Am. J. Physiol.* Vol. 261, No. 6 Pt. 1, December 1991, pages C1081–C1090.

47. Gerhardstein B L, et al.: Proteolytic processing of the C terminus of the alpha (1C) subunit of L-type calcium channels and role of a proline-rich domain in membrane tethering of proteolytic fragments. *J Biol. Chem.* Vol. 275, No. 12, Mar. 24, 2000, pages 8556–8563.

48. Barbuti A, et al.: Action of internal pronase on the f-channel kinetics in the rabbit SA node. *J. Physiol.* Vol. 520, No. 3, Nov. 1, 1999, pages 737–744.

49. Wainger B J, et al.: Domains involved in cyclic nucleotide modulation of hyperpolarization-activated HCN channels. *Nature*. In Press, 2001.

50. Wahler G M: Developmental increases in the inwardly rectifying potassium current of rat ventricular myocytes. *Am. J. Physiol.* Vol. 262, No. 5 Pt. 1, May 1992, pages C1266.

51. Abbott G W, et al.: MiRP1 forms $I_{kr}$ potassium channels with HERG and is associated with cardiac arrhythmia. *Cell.* Vol. 97, No. 2, Apr. 16, 1999, pages 175–187.

52. Sanguinetti M C, et al.: Coassembly of KvLGQT1 and minK ($I_{SK}$) proteins to form cardiac $I_{SK}$ potassium channels. *Nature*. Vol. 384, No. 6604, Nov. 7, 1996, pages 80–83.

53. Dixon J E and McKinnon D: Quantitative analysis of potassium channel expression in atrial and ventricular muscle of rats. *Circ. Res.* Vol. 75, No. 2, August 1994, pages 252–260.

54. Sclagger H and von Jagow G: Tricine-sodium dodecyl sulfate-polyacrylamide gel electrophoresis for separation of proteins in the range from 1 to 100 Kda. *Analytical Biochem.* Vol. 166, No. 2, Nov. 1, 1987, pages 368–379.

55. Hansen J E, et al.: Prediction of O-glycosylation of mammalian proteins:Specificity patterns of UDP-GalNAc:polypeptide N-acetylgalactosaminyltransferase. *Biochem. J.* Vol. 308, No. 3, Jun. 15, 1995, pages 801–813.

56. Vassalle M, et al.: Pacemaker channels and cardiac automaticity In "Cardiac Electrophysiology. From Cell to Bedside", Eds. Zipes D and Jalife W B Saunders Co. Philadelphia, Pa., 2000, pages 94–103.

What is claimed:

1. A method of increasing the heart rate of a subject having a cardiac condition which comprises contacting a cell of the heart of the subject by injection or catheterization with a composition comprising a nucleic acid encoding MiRP1 and HCN2 in an amount sufficient to increase the pacemaker current expression of the cell, thereby increasing the heart rate.

2. The method of claim 1, wherein the subject is a mammal.

3. The method of claim 2, wherein the mammal is a human.

4. The method of claim 1, wherein the cell is a cardiac myocyte.

5. The method of claim 1, wherein the method is performed on a subject having a cardiac condition selected from the group consisting of bradycardia, complete atrioventricular block, incomplete atrioventricular block, heart block and sinus node dysfunction.

6. A method of inducing a pacemaker current in a cell of the heart of a subject which comprises contacting a cell of the heart of the subject by injection or catheterization with a compound comprising a nucleic acid encoding HCN2 and MiRP1 in a sufficient amount to induce the pacemaker current in the cell of the heart of the subject, thereby inducing a pacemaker current in the cell of the heart of the subject.

7. The method of claim 1, wherein the composition is an adenovirus, a virus or a liposome.

* * * * *